United States Patent
Lascola et al.

(10) Patent No.: US 12,331,032 B2
(45) Date of Patent: Jun. 17, 2025

(54) QUINONE REDUCTASE 2 INHIBITOR COMPOUNDS AND USES THEREOF

(71) Applicant: DUKE UNIVERSITY, Durham, NC (US)

(72) Inventors: Christopher D. Lascola, Durham, NC (US); Daniel T. Laskowitz, Chapel Hill, NC (US)

(73) Assignee: DUKE UNIVERSITY, Durham, NC (US)

( * ) Notice: Subject to any disclaimer, the term of this patent is extended or adjusted under 35 U.S.C. 154(b) by 867 days.

(21) Appl. No.: 17/285,622

(22) PCT Filed: Oct. 16, 2019

(86) PCT No.: PCT/US2019/056534
§ 371 (c)(1),
(2) Date: Apr. 15, 2021

(87) PCT Pub. No.: WO2020/081680
PCT Pub. Date: Apr. 23, 2020

(65) Prior Publication Data
US 2021/0395220 A1 Dec. 23, 2021

Related U.S. Application Data

(60) Provisional application No. 62/746,870, filed on Oct. 17, 2018.

(51) Int. Cl.
| | | |
|---|---|---|
| C07D 401/12 | (2006.01) | |
| A61K 31/4709 | (2006.01) | |
| C07D 215/02 | (2006.01) | |

(52) U.S. Cl.
CPC ......... *C07D 401/12* (2013.01); *C07D 215/02* (2013.01); *A61K 31/4709* (2013.01)

(58) Field of Classification Search
CPC . C07D 401/12; C07D 215/02; A61K 31/4709
See application file for complete search history.

(56) References Cited

U.S. PATENT DOCUMENTS

| | | |
|---|---|---|
| 6,680,299 B2 | 1/2004 | Or et al. |
| 6,680,322 B2 | 1/2004 | Castelhano et al. |
| 6,680,324 B2 | 1/2004 | Castelhano et al. |
| 2006/0074105 A1* | 4/2006 | Ware, Jr. ............... C07D 401/12 546/159 |

FOREIGN PATENT DOCUMENTS

| | | | | |
|---|---|---|---|---|
| CN | 101528743 A | 9/2009 | | |
| JP | 2009543789 A | 12/2009 | | |
| WO | WO-2006034235 A2 * | 3/2006 | .......... | C07D 215/18 |
| WO | 2008008539 A2 | 1/2008 | | |

OTHER PUBLICATIONS

Patani (Dec. 19, 1996) Bioisosterism A rational approach in drug design, Chem. Rev., 96, 3147-3176 (Year: 1996).*
Boezio et. al., (Sep. 27, 2009), Discovery and optimization of potent and selective triazolopyridazine series of c-Met inhibitors, Bioorg Med Chem Lett, 19, 6307-6312 (Year: 2009).*
Patani et. al. (Dec. 19, 1996) Bioisosterism A rational approach in drug design, Chem. Rev., 96, 3147-3176 (Year: 1996).*
Cassagnes, Laure-Estelle, et al., "Oxidative stress and neurodegeneration: The possible contribution of quinone reductase 2", Free Radic. Bio. Med. 120, 2018, 56-61.
Egan, Timothy J., et al., "Interactions of quinoline antimalarials with hematin in solution", J. Inorg. Biochem. 100 (5-6), 2006, 916-926.
Egan, Timothy J., et al., "Structure-Function Relationships in Aminoquinolines: Effect of Amino and Chloro Groups on Quinoline—Hematin Complex Formation, Inhibition of β-Hematin Formation, and Antiplasmodial Activity", J. Med. Chem. 43(2), 2000, 283-291.
Foley, Michael, et al., "Quinoline Antimalarials: Mechanisms of Action and Resistance and Prospects for New Agents", Pharmacol. Ther. 79(1), 1998, 55-87.
Kaschula, Catherine H., et al., "Structure—Activity Relationships in 4-Aminoquinoline Antiplasmodials. The Role of the Group at the 7-Position", J. Med. Chem. 45(16), 2002, 3531-3539.
Singer, N. G., et al., "Update on immunosuppressive therapy", Curr. Opin. Rheumatol. 10(3), 1998, 169-173.
Vippagunta, Sudha Rani, et al., "Structural Specificity of Chloroquine—Hematin Binding Related to Inhibition of Hematin Polymerization and Parasite Growth", J. Med. Chem. 42(22), 1999, 4630-4639.
Japanese Office Action corresponding to JP 2021-521206; dated Sep. 29, 2023 (9 pages, including English translation).
Canadian Office Action corresponding to CA 3,114,462; dated Jan. 26, 2024 (4 pages).
Second Chinese Office Action corresponding to CN 201980068516.0; dated Nov. 23, 2023 (16 pages, including English translation).

(Continued)

*Primary Examiner* — Juliet C Switzer
*Assistant Examiner* — Dawanna Shar-Day White
(74) *Attorney, Agent, or Firm* — Myers Bigel, P.A.

(57) ABSTRACT

Provided herein according to some embodiments is a compound of Formula (I): [Formula], or a pharmaceutically acceptable salt or prodrug thereof. Compositions comprising the compound, and uses thereof for inhibiting the activity of quinone reductase-2, as well as in methods of treatment, are also provided.

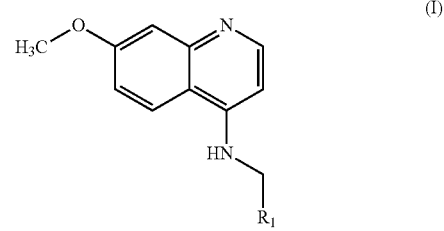

24 Claims, 9 Drawing Sheets

(56) References Cited

OTHER PUBLICATIONS

International Search Report and Written Opinion corresponding to PCT/US2019/056534; dated Dec. 10, 2019 (14 pages).
Boezio, Alessandro A., et al., "Discovery and optimization of potent and selective triazolopyridazine series of c-Met inhibitors", Bioorganics & Medicinal Chemistry Letters 19(22), 2009, 6307-6312.
Boutin, Jean A., et al., "S29434, a Quinone Reductase 2 Inhibitor: Main Biochemical and Cellular Characterization", Mol. Pharma 95(3), 2019, 269-285.
Giulian, Dana, "Microglia and the Immune Pathology of Alzheimer Disease", Am. J. Hum. Genet. 65, 1999, 13-18.
Giulian, Dana, et al., "The role of mononuclear phagocytes in wound healing after traumatic injury to adult mammalian brain", J. Neurosci. 9(12), 1989, 4416-4429.
Harada, Shoji, et al., "An Association between Idiopathic Parkinson's Disease and Polymorphisms of Phase II Detoxification Enzymes: Glutathione S-Transferase M1 and Quinone Oxidoreductase 1 and 2", Biochem Biophys Res Commun 288(4), 2001, 887-892.
Ivanova, Svetlana, et al., "Cerebral Ischemia Enhances Polyamine Oxidation: Identification of Enzymatically Formed 3-Aminopropanal as an Endogenous Mediator of Neuronal and Glial Cell Death", J. Exp. Med. 188(2), 1998, 327-340.
Janda, Elzbieta, et al., "Parkinsonian toxin-induced oxidative stress inhibits basal autophagy in astrocytes via NQO2/quinone oxidoreductase 2: Implications for neuroprotection", Autophagy 11(7), 2015, 1063-1080.
Janda, Elzbieta, et al., "The antidote effect of quinone oxidoreductase 2 inhibitor against paraquat-induced toxicity in vitro and in vivo", BJP 168(1), 2013, 46-59.
Jung, Hyejung, et al., "The protective effect of antimalarial drugs on thrombovascular events in systemic lupus erythematosus", Arthritis Rheum. 62(3), 2010, 863-868.
Laskowitz, Daniel T., et al., "Neuroprotective pentapeptide CN-105 is associated with reduced sterile inflammation and improved functional outcomes in a traumatic brain injury murine model", Sci. Rep. 7:46461, 2017.
Laskowitz, Daniel T., et al., "Traumatic Brain Injury Exacerbates Neurodegenerative Pathology: Improvement with an Apolipoprotein E-Based Therapeutic", J. Neurotrauma 27(11), 2010, 1983-1995.
Nicolson, Garth L., "Mitochondrial Dysfunction and Chronic Disease: Treatment With Natural Supplements", Integrative Medicine 13(4), 2014, 35-43.
Sanders, Laurie H., et al., "Oxidative damage to macromolecules in human Parkinson disease and the rotenone model", Free Radic. Bio. Med. 62, 2013, 111-120.
Savarino, Adrea, et al., "Effects of chloroquine on viral infections: an old drug against today's diseases", Lancet Infect. Dis. 3(11), 2003, 722-727.
Sharma, Tarus S., et al., "Hydroxychloroquine Use Is Associated With Decreased Incident Cardiovascular Events in Rheumatoid Arthritis Patients", J. Amer. Heart Assoc. 5(1), 2016, e002867.
Sotelo, Julio, et al., "Adding Chloroquine to Conventional Treatment for Glioblastoma Multiforme: A Randomized, Double-Blind, Placebo-Controlled Trial", Ann. Intern. Med. 144(5), 2006, 337-343.
Spencer, Diane M., et al., "The properties of microparticles from RAW 264.7 macrophage cells undergoing in vitro activation or apoptosis", Innate Immunity 20(3), 2014, 239-248.
Tanner, Caroline M., et al., "Rotenone, paraquat, and Parkinson's disease", Environ Health Perspectives 119(6), 2011, 866-872.
Wallace, Daniel J., et al., "The Relevance of Antimalarial Therapy with Regard to Thrombosis, Hypercholesterolemia and Cytokines in SLE", Lupus 2(Suppl 1), 1993, S13-S15.
Wallace, DJ, "The use of chloroquine and hydroxychloroquine for non-infectious conditions other than rheumatoid arthritis or lupus: a critical review", Lupus 5(Suppl 1), 1996, S59-S64.
Wang, Wei, et al., "Association of NRH:Quinone Oxidoreductase 2 Gene Promoter Polymorphism With Higher Gene Expression and Increased Susceptibility to Parkinson's Disease", J. Gerontol.: Series A 63(2), 2008, 127-134.
European Examination Report corresponding to 19798790.2; dated Jan. 26, 2023 (4 pages).
First Chinese Office Action corresponding to CN 201980068516.0; dated Apr. 4, 2023 (29 pages, including English translation).
Australian Examination Report No. 1 corresponding to AU 2019362848; dated Apr. 9, 2024 (3 pages).
Decision of Rejection corresponding to JP Application No. 2021-521206; dated May 8, 2024 (6 pages, including English translation).
Decision on Rejection issued in corresponding Chinese Application No. 201980068516.0, mailed Apr. 19, 2024 (23 pages, including English translation).
European Examination Report corresponding to 19798790.2; dated Sep. 15, 2023 (4 pages).
Australian Examination Report No. 2 corresponding to AU 2019362848; dated Nov. 11, 2024 (3 pages).
Canadian Office Action corresponding to CA 3114462; dated Oct. 15, 2024 (3 pages).
Pre-Appeal Initial Review Report corresponding to JP Appeal No. 2024-014444; dated Nov. 14, 2024 (7 pages, including English translation).
Deshpande, Shreekant, et al., "4-aminoquinolines: An Overview of Antimalarial Chemotherapy", Medicinal chemistry 6(1): 001-011, 2016.
Iskander, Karim, et al., "NQO1 and NQO2 Regulation of Humoral Immunity and Autoimmunity", The Journal of Biological Chemistry 281(41): 30917-30924, 2006.
Kwiek, Jesse J., et al., "Kinetic Mechanism of Quinone Oxidoreductase 2 and Its Inhibition by the Antimalarial Quinolines", Biochemistry 43: 4538-4547, 2004.
Leung, Kevin K. K., et al., "Chloroquine Binding Reveals Flavin Redox Switch Function of Quinone Reductase 2", The Journal of Biological Chemistry 288(16): 11242-11251, 2013.

* cited by examiner

QUINONE REDUCTASE 2 INHIBITOR COMPOUNDS AND USES THEREOF

CROSS REFERENCE TO RELATED APPLICATIONS

This application is a 35 U.S.C. § 371 national phase application of International Application Serial No. PCT/US2019/056534, filed Oct. 16, 2019, which claims the benefit of U.S. provisional patent application Ser. No. 62/746,870, filed Oct. 17, 2018, the disclosure of which is incorporated by reference herein in its entirety.

STATEMENT OF GOVERNMENT SUPPORT

This invention was made in part with government support under grant number W81XWH-12-1-0447 awarded by the Department of Defense. The United States government has certain rights in the invention.

BACKGROUND

Aminoquinolines, with chloroquine (CQ) and hydroxychloroquine (HQ) as prototypes, are quinone reductase 2 (QR2) inhibitors that were originally developed to treat malaria but were subsequently found to have therapeutic efficacy for other indications, including, inter alia, autoimmune diseases such as systemic lupus erythematosis (SLE) and rheumatoid arthritis (RA). Singer et al., "Update on immunosuppressive therapy," *Curr. Opin. Rheumatol.* 1998, 10:169-173; Wallace, "The use of chloroquine and hydroxychloroquine for non-infectious conditions other than rheumatoid arthritis or lupus: a crucial review," *Lupus* 1996, 5 Suppl 1:S59-64. In SLE and RA, aminoquinolines are a mainstay of first-line therapy and are often used in combination with other medications. Aminoquinolines not only improve the signs and symptoms of SLE and RA but also have beneficial effects on lipid metabolism and reduce the occurrence of thrombosis. In patients with inflammatory or erosive osteoarthritis, similar benefits are observed. Efficacy has also been shown when used as adjunctive therapy in graft-vs-host disease, cancer, and HIV. Savarino et al., "Effects of chloroquine on viral infections: an old drug against today's diseases?" *Lancet Infect. Dis.* 2003, 3(11): 722-7; Savarino et al., "Risks and benefits of chloroquine use in anticancer strategies," *Lancet Oncol.* 2006, 7(10): 792-3; Sotelo et al., "Adding chloroquine to conventional treatment for glioblastoma multiforme: a randomized, double-blind, placebo-controlled trial," *Ann. Intern. Med.* 2006, 144(5):337-43.

The potential for chloroquine (CQ) in neuroprotection has been studied previously in preclinical models of stroke, excitotoxic and traumatic injuries, although the therapeutic mechanisms have remained elusive. CQ dramatically limits microglial and PMN migration into injury sites in the brain, decreases reactive astrogliosis and neovascularization, and reduces stroke volumes by 60% in a permanent MCA occlusion model. Giulian et al., "The role of mononuclear phagocytes in wound healing after traumatic injury to adult mammalian brain," *J. Neurosci.* 1989, 9:4416-4429; Ivanova et al., "Cerebral ischemia enhances polyamine oxidation: identification of enzymatically formed 3-aminopropanal as an endogenous mediator of neuronal and glial cell death," *J. Exp. Med.* 1998, 188:327-340. CQ also decreases cytokine production by microglial cells in vitro in response to various irritants. Giulian, "Microglia and the immune pathology of Alzheimer disease," *Am. J. Hum. Genet.* 1999, 65:13-18.

Because some malaria is resistant to CQ, derivative compounds have also been explored. For example, US 2006/0074105 to Ware et al. describes certain quinoline and quinazoline derivatives said to be useful in the treatment of malaria and autoimmune diseases.

Though CQ and HQ are often used clinically as a first-line therapy in autoimmune disorders, their efficacy is limited by serious side effects. The most important and best-characterized toxicity is retinal, where long-term use may lead to "bull's eye maculopathy" and blindness unless dosing is limited. Cardiac toxicity, although rare, may also occur, manifesting either as conduction disturbances (e.g., bundle-branch block) and/or cardiomyopathy in association with congestive heart failure. Electron microscopy of cardiac and retinal biopsies after long-term CQ or HQ therapy reveals pathognomonic cytoplasmic inclusion bodies, understood to be a direct consequence of high drug accumulation in lysosomes (and melanosomes in retina and skin). Remarkably, CQ is capable of accumulating to mM concentration in skin, retinal, renal, and liver cells during therapeutic dosing while plasma concentrations remain <1 µM.

There remains a need to develop additional aminoquinoline quinone reductase 2 (QR2) inhibitors, particularly that also have diminished lysosomal accumulation in order to reduce toxicity.

SUMMARY

Provided herein according to some embodiments is a compound of Formula (I):

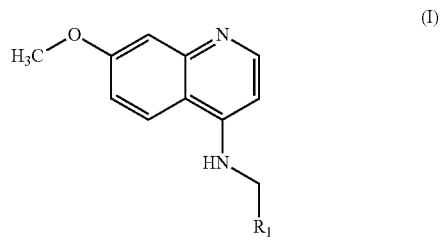

wherein:

$R_1$ is a nitrogen-containing heterocyclo or a nitrogen-containing heteroaryl, wherein said compound is optionally substituted one, two or three times with fluoromethyl, difluoromethyl or trifluoromethyl, or a pharmaceutically acceptable salt or prodrug thereof.

In some embodiments, $R_1$ is:

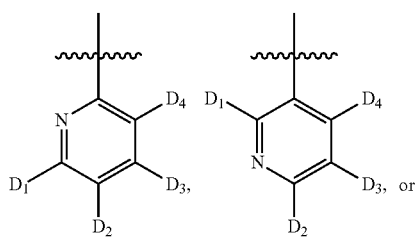

-continued

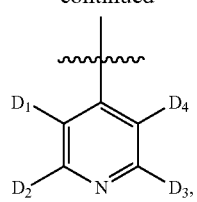

wherein $D_1$, $D_2$, $D_3$, and $D_4$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or $D_1$ and $D_2$, $D_2$ and $D_3$, or $D_3$ and $D_4$ together form a fused ring (e.g., a cyclohexane or cyclohexene fused ring) that is optionally substituted, wherein said compound (inclusive of $R_1$) may be optionally substituted one, two or three times with fluoromethyl, difluoromethyl or trifluoromethyl, or a pharmaceutically acceptable salt or prodrug thereof.

In some embodiments, $D_1$, $D_2$, $D_3$, and $D_4$ are each hydrogen.

In some embodiments, the compound is a compound of Formula (I)(a)(1) or a compound of Formula (I)(a)(2):

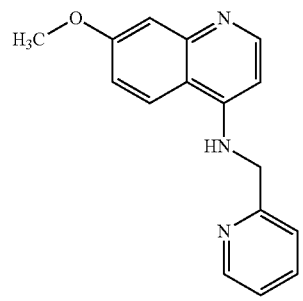

(I)(a)(1)

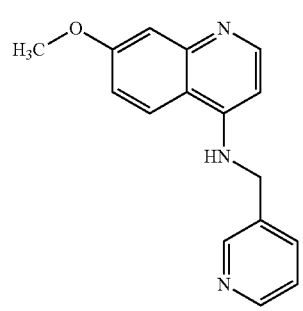

(I)(a)(2)

wherein said compound is optionally substituted one, two or three times with fluoromethyl, difluoromethyl or trifluoromethyl, or a pharmaceutically acceptable salt or prodrug thereof.

In some embodiments, the compound is a compound of Formula (I)(a)(2):

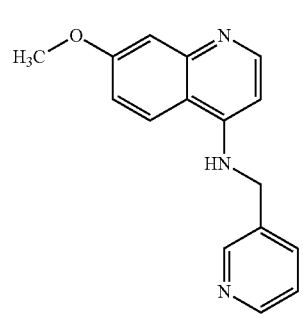

(I)(a)(2)

wherein said compound is optionally substituted one, two or three times with fluoromethyl, difluoromethyl or trifluoromethyl, or a pharmaceutically acceptable salt or prodrug thereof.

In some embodiments, the compound is a compound of Formula (I)(a)(2):

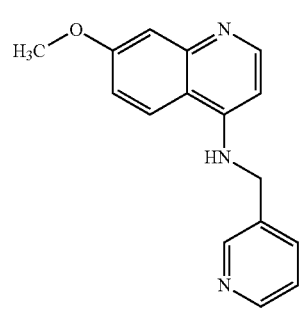

(I)(a)(2)

or a pharmaceutically acceptable salt or prodrug thereof.

In some embodiments, $R_1$ is:

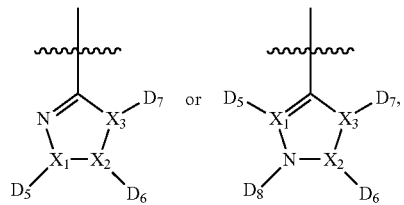

wherein $X_1$, $X_2$, and $X_3$ are each independently selected from the group consisting of carbon, nitrogen, and oxygen, and when present, $D_5$, $D_6$, $D_7$, and $D_8$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_5$, $D_6$, $D_7$, and $D_8$ together form a fused ring (e.g., a cyclohexane or cyclohexene fused ring) that is optionally substituted, wherein said compound is optionally substituted one, two or three times with fluoromethyl, difluoromethyl or trifluoromethyl, or a pharmaceutically acceptable salt or prodrug thereof.

In some embodiments, the compound is a compound of Formula (I)(b)(1):

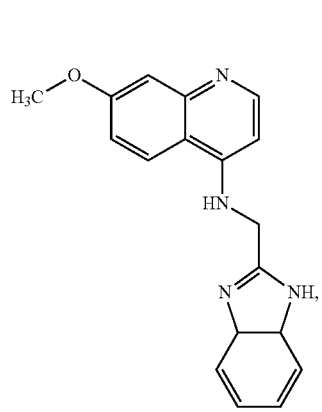

(I)(b)(1)

wherein said compound is optionally substituted one, two or three times with fluoromethyl, difluoromethyl or trifluoromethyl,
or a pharmaceutically acceptable salt or prodrug thereof
In some embodiments, $R_1$ is:

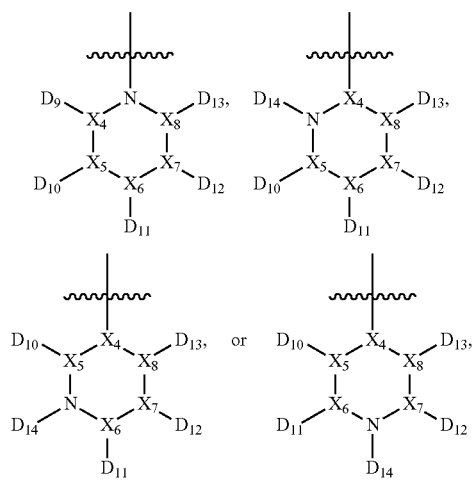

wherein $X_4$, $X_5$, $X_6$, $X_7$, and $X_8$ are each independently selected from the group consisting of carbon, nitrogen, and oxygen, wherein at least two or at least three of said $X_4$, $X_5$, $X_6$, $X_7$, and $X_8$ are carbon, and when present, $D_9$, $D_{10}$, $D_{11}$, $D_{12}$, $D_{13}$, and $D_{14}$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_9$, $D_{10}$, $D_{11}$, $D_{12}$, $D_{13}$, and $D_{14}$ together form a fused ring (e.g., a cyclohexane or cyclohexene fused ring) that is optionally substituted,
wherein said compound is optionally substituted one, two or three times with fluoromethyl, difluoromethyl or trifluoromethyl,
or a pharmaceutically acceptable salt or prodrug thereof.

In some embodiments, $R_1$ is:

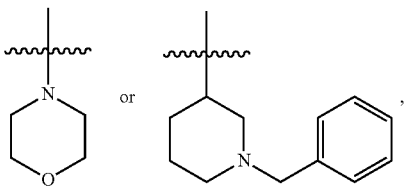 [SMILES: *N1CCOCC1 ; *C1CCCN(Cc2ccccc2)C1]

wherein said compound is optionally substituted one, two or three times with fluoromethyl, difluoromethyl or trifluoromethyl,
or a pharmaceutically acceptable salt or prodrug thereof.
In some embodiments, $R_1$ is:

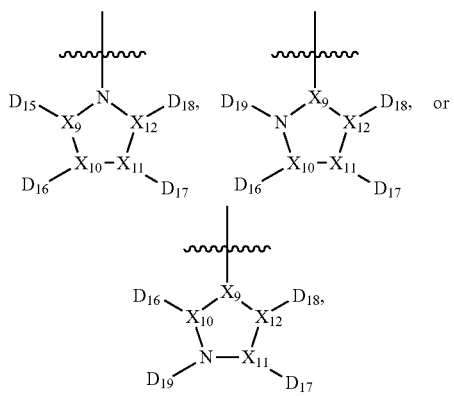

$X_9$, $X_{10}$, $X_{11}$, and $X_{12}$ are each independently selected from the group consisting of carbon, nitrogen, and oxygen, wherein at least two of said $X_9$, $X_{10}$, $X_{11}$, and $X_{12}$ are carbon, and when present, $D_{15}$, $D_{16}$, $D_{17}$, $D_{18}$, and $D_{19}$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_{15}$, $D_{16}$, $D_{17}$, $D_{18}$, and $D_{19}$ together form a fused ring (e.g., a cyclohexane or cyclohexene fused ring), optionally substituted,
wherein said compound is optionally substituted one, two or three times with fluoromethyl, difluoromethyl or trifluoromethyl,
or a pharmaceutically acceptable salt or prodrug thereof.
In some embodiments, $R_1$ is:

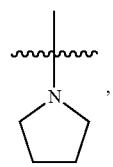

wherein said compound is optionally substituted one, two or three times with fluoromethyl, difluoromethyl or trifluoromethyl,
or a pharmaceutically acceptable salt or prodrug thereof.
In some embodiments, the compound has a positive log D value at approximately pH 4 to pH 5.

Also provided is a composition comprising a compound as described herein and a carrier (e.g., a pharmaceutically acceptable carrier).

Further provided is a method for inhibiting the activity of quinone reductase-2 (QR2), comprising contacting QR2 with a compound or composition as taught herein, wherein said contacting is performed in vitro, or wherein said contacting is performed in vivo.

Also provided is a method of treatment for malaria in a subject in need thereof, comprising administering to said subject in a treatment-effective amount a compound or composition as taught herein. Further provided is a compound or composition as taught herein for use in treating malaria. Still further provided is the use of a compound as taught herein for the preparation of a medicament for the treatment of malaria.

Also provided is a method of treatment for an immune disorder in a subject in need thereof, comprising administering to said subject in a treatment-effective amount a compound or composition as taught herein. Further provided is a compound or composition as taught herein for use in treating an immune disorder. Still further provided is the use of a compound as taught herein for the preparation of a medicament for the treatment of an immune disorder.

Also provided is a method of treatment for an acute neural injury in a subject in need thereof, comprising administering to said subject in a treatment-effective amount a compound or composition as taught herein. Further provided is a compound or composition as taught herein for use in treating an acute neural injury. Still further provided is the use of a compound as taught herein for the preparation of a medicament for the treatment of an acute neural injury.

Also provided is a method of treatment for a chronic neurological disorder (e.g., Parkinson's disease or Alzheimer's disease) in a subject in need thereof, comprising administering to said subject in a treatment-effective amount a compound or composition as taught herein. Further provided is a compound or composition as taught herein for use in treating a chronic neurological disorder. Still further provided is the use of a compound as taught herein for the preparation of a medicament for the treatment of a chronic neurological disorder.

Also provided is a method of treatment for lupus in a subject in need thereof, comprising administering to said subject in a treatment-effective amount a compound or composition as taught herein. Further provided is a compound or composition as taught herein for use in treating lupus. Still further provided is the use of a compound as taught herein for the preparation of a medicament for the treatment of lupus.

Also provided is a method of treatment for an infectious disease in a subject in need thereof, comprising administering to said subject in a treatment-effective amount a compound or composition as taught herein. Further provided is a compound or composition as taught herein for use in treating an infectious disease. Still further provided is the use of a compound as taught herein for the preparation of a medicament for the treatment of an infectious disease.

Also provided is a method of treatment for cancer in a subject in need thereof, comprising administering to said subject in a treatment-effective amount a compound or composition as taught herein. Further provided is a compound or composition as taught herein for use in treating cancer. Still further provided is the use of a compound as taught herein for the preparation of a medicament for the treatment of cancer.

Also provided is a method of treatment for CNS lupus in a subject in need thereof, comprising administering to said subject in a treatment-effective amount a compound or composition as taught herein. Further provided is a compound or composition as taught herein for use in treating CNS lupus. Still further provided is the use of a compound as taught herein for the preparation of a medicament for the treatment of CNS lupus.

Also provided is a method of treatment for a subject at increased risk for cerebrovascular disease, comprising administering to said subject in a treatment-effective amount a compound or composition as taught herein. Further provided is a compound or composition as taught herein for use in treating a subject at increased risk for cerebrovascular disease. Still further provided is the use of a compound as taught herein for the preparation of a medicament for the treatment of a subject at increased risk for cerebrovascular disease.

In some embodiments of the above methods or uses, the administering comprises chronic administration (e.g., over several months or years).

In some embodiments of the above methods or uses, the administering is performed once daily.

BRIEF DESCRIPTION OF THE DRAWINGS

FIG. 1A shows a graph of log D versus pH for chloroquine. The log D of chloroquine below pH 6 is negative, consistent with loss of membrane permeability. FIG. 1B shows a graph of log D versus pH for QR2I-44. The log D of QR2I-44 above about pH 4 is positive, indicating retained membrane permeability in the range of lysosomal pH. Unlike CQ, QR2I-44 is not trapped in lysosomes.

FIG. 2A presents 5 day rotorod results of QR2I-44 versus vehicle. FIG. 2B presents 5 day rotorod results of QR2I-44 versus chloroquine (CQ). Results show that QR2I-44 is neuroprotective following TBI and therapeutically superior to CQ.

FIG. 5A shows speed versus days post traumatic brain injury (TBI) with the administration of QR2I-44 in a Morris Water Maze (MWM) test. The results indicate that the effect seen in FIG. 5B (i.e., faster learning with QR2I-44 administration) is not compromised by differences in motor ability. P-value=0.0165, significance level=5%.

FIG. 6A is a representative high resolution coronal MRI of mouse brain with hippocampal ROI overlay for volumetric analyses. FIG. 6B is a graph of hippocampus volumes in normal, treated and untreated groups, showing statistically significant improvement in volumes in mice treated with QR2I-44 versus vehicle controls.

FIG. 7A is a representative MRI with template overlay ROIs of critical subcortical brain structures, including corpus collosum/external capsule (CC/EC). FIG. 7B is a graph of fractional anisotropy (FA) of CC/EC in normal, treated and untreated groups following TBI, revealing improvements in FA of these large white matter tracts following QR2I-44 therapy. FA is a general measure of tract integrity using a high resolution MRI technique called diffusion tensor imaging (DTI).

FIG. 8A shows results of inflammatory microparticle (MP) release from RAW 264.7 cells following stimulation with TOLL receptor ligand and treatment with QR2I-44. FIG. 8B and FIG. 8C show results of TNF alpha release from RAW 264.7 cells following stimulation with TOLL receptor ligands and treatment with QR2I-44. Toll Receptor Ligands: PIC=polyinosinic:polycytidylic acid (TLR3); CpG=CpG oligodeoxynucleotide DNA (TLR9).

DETAILED DESCRIPTION

Figure 1A:
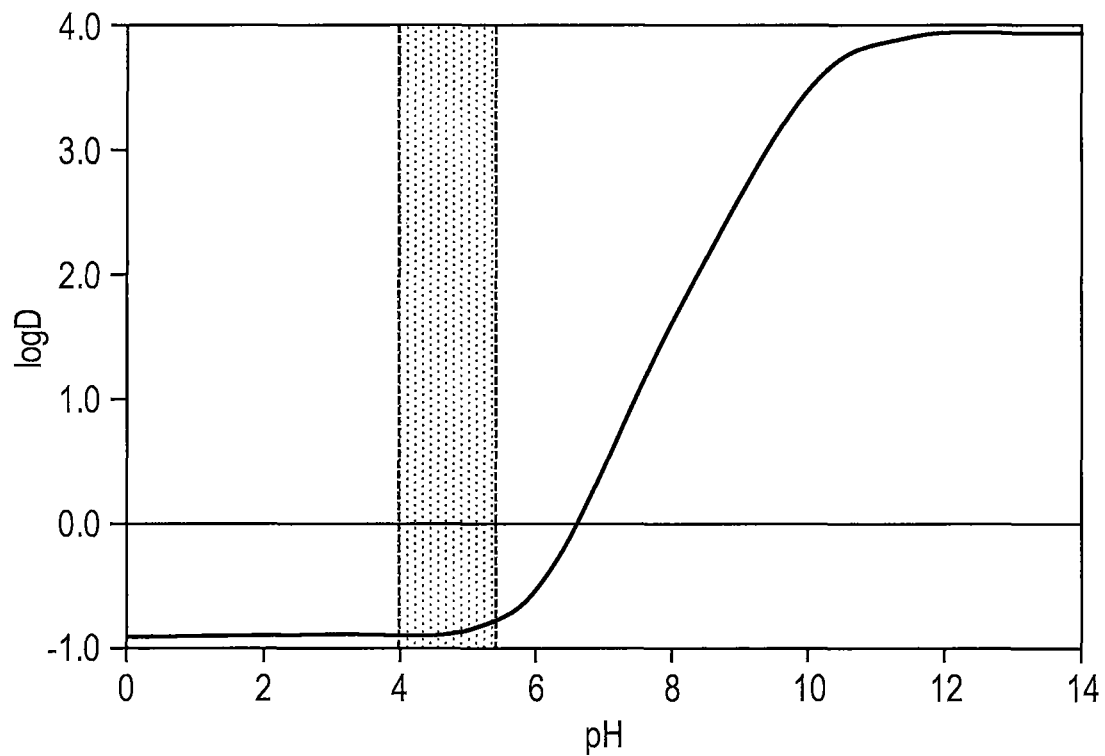
FIG. 1A-FIG. 1B.

Provided herein are compounds useful as inhibitors of quinone reductase-2, as well as formulations and methods of use thereof. In some embodiments, the compounds are useful in the treatment of infectious diseases, cancer, immune disorders, acute neural injury and chronic neurological disorders, as well as subjects at increased risk for cerebrovascular disease.

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" and "I" refer to and encompass any and all possible combinations of one or more of the associated listed items, as well as the lack of combinations when interpreted in the alternative ("or").

I. Definitions

The following definitions are used herein.

As known in the art, "H" refers to a hydrogen atom. "C" refers to a carbon atom. "N" refers to a nitrogen atom. "O" refers to an oxygen atom.

"Halo" refers to F, Cl, Br or I. "Cl" is chloro, "I" is iodo, "F" is fluoro, and "Br" is bromo.

An "acyl" is a group —C(O)R, where R is a suitable substituent (for example, an acetyl group, a propionyl group, a butyroyl group, a benzoyl group, or an alkylbenzoyl group).

"Alkyl," as used herein, refers to a straight or branched chain saturated hydrocarbon containing from 1 or 2 to 10 or 20 or more carbon atoms (e.g., C2, C3, C4, C5, C6, C7, C8, C9, C10, C11, C12, C13, C14, C15, etc.). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, the alkyl is a "lower alkyl" having from 1 to 3, 4, or 5 carbon atoms.

"Alkenyl" as used herein is a straight or branched chain unsaturated hydrocarbon group having one or more double bonds.

"Alkynyl" as used herein is a straight or branched chain unsaturated hydrocarbon group having one or more triple bonds.

"Amino" is the group —NH$_2$. An "amide" as used herein refers to an organic functional group having a carbonyl group (C=O) linked to a nitrogen atom (N).

"Alkoxy," as used herein, refers to an alkyl group, as defined herein, appended to the parent molecule through an oxygen atom (—O—). Representative examples of alkoxy include, but are not limited to, methoxy, ethoxy, propoxy, 2-propoxy, butoxy, tert-butoxy, pentyloxy, hexyloxy and the like.

"Aryl" as used herein refers to a ring system having one or more aromatic rings. Representative examples of aryl include azulenyl, indanyl, indenyl, naphthyl, phenyl, tetrahydronaphthyl, and the like.

"Haloalkyl," as used herein, a refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.) in which at least one of the hydrogen atoms have been replaced with halo (F, Cl, Br or I). Representative examples of "haloalkyl" include, but are not limited to, fluoroalkyl (e.g., fluoromethyl (—CH$_2$F), difluoromethyl (—CHF$_2$), or trifluoromethyl (—CF$_3$)).

"Heterocyclo," as used herein, refers to a monocyclic, bicyclic or tricyclic ring system containing at least one heteroatom selected from O, N, and S. Monocyclic heterocycle ring systems are exemplified by any 5 or 6 member ring containing 1, 2, 3, or 4 heteroatoms independently selected from the group consisting of: 0, N, and S. The 5 member ring has from 0 to 2 double bonds, and the 6 member ring has from 0 to 3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. Examples of nitrogen-containing heterocyclo include, but are not limited to, pyrrolidinyl, piperidinyl, piperazinyl, morpholinyl, etc.

"Heteroaryl" means a cyclic, aromatic hydrocarbon in which one or more carbon atoms have been replaced with atoms independently selected from the group consisting of: O, N, and S. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O. Examples of nitrogen-containing heteroaryls include, but are not limited to, pyridinyl, pyrimidinyl, pyrazinyl, pyridazinyl, imidazolyl, pyrrolyl, pyrazolyl, thiazolyl, triazolyl, isothiazolyl, indolyl, benzimidazolyl, benzoxazolyl, quinolinyl, isoquinolinyl, quinazolinyl, acridinyl, carbazole, azepinyl, 1,4-diazepinyl, purinyl, pteridinyl, phthalazinyl, etc.

The aryl, heteroaryl, and heterocyclo groups of this invention may be substituted 1, 2, 3, 4, or 5 times, as chemically feasible, with substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halo, haloalkyl, haloalkoxy, hydroxy, hydroxyalkyl, mercapto, nitro, sulfamyl, sulfo, sulfonate, NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Hydroxyl" and "hydroxy" refer to the group —OH.

"Nitrile" refers to the group —CN.

"Nitro" refers to the group —NO$_2$.

A "sulfone" refers to a sulfonyl functional group, —SO$_2$R, wherein R is any covalently linked atom or atoms.

A "sulfoxide" refers to the group —S(O)R, wherein R is any covalently linked atom or atoms.

A "thiol" or "mercapto" refers to the group —SH or to its tautomer =S.

"Fused ring" as used herein refers to a ring system (e.g., "heterocyclo," "aryl," or "heteroaryl") that may be formed by two substituents of a formula as provided herein. Each of two substituents may together form part of a ring system, as illustrated below as Fused ring I or Fused ring II for example substituents R$_2$ and R$_3$, which may be independently selected C, O, N or S. Carbons included in Fused ring II may also be substituted by heteroatoms independently selected from the group consisting of: O, N, and S. The fused ring system, including each heteroatom, when present, can be unsubstituted or substituted with 1 to 4 suitable substituents, as chemically feasible.

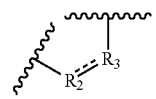

Fused ring I

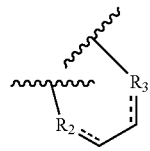

Fused ring II

A "pharmaceutically acceptable salt" is a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

A "prodrug" as known in the art is a compound that can be converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entireties. See also U.S. Pat. No. 6,680,299. Examples include a prodrug that is metabolized in vivo by a subject to an active compound as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

As understood in the art, the term "optionally substituted" indicates that the specified group is either unsubstituted, or substituted by one or more suitable substituents. A "substituent" that is "substituted" is a group which takes the place of a hydrogen atom on the parent organic molecule.

II. Active Compounds

Provided herein as an active compound is a compound of Formula (I):

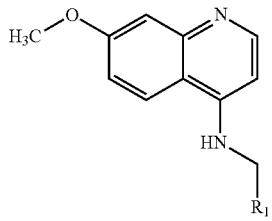
(I)

wherein:

R₁ is a nitrogen-containing heterocyclo or a nitrogen-containing heteroaryl, or a pharmaceutically acceptable salt or prodrug thereof. In some embodiments, the compound may be substituted one, two or three times, with independently selected suitable groups such as fluoromethyl, difluoromethyl or trifluoromethyl.

In some embodiments, R₁ is:

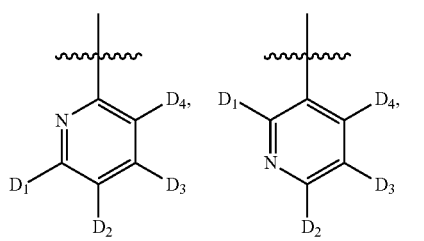

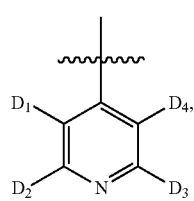

wherein $D_1$, $D_2$, $D_3$, and $D_4$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or $D_1$ and $D_2$, $D_2$ and $D_3$, or $D_3$ and $D_4$ together form a fused ring (e.g., a cyclohexane or cyclohexene fused ring) that is optionally substituted, or a pharmaceutically acceptable salt or prodrug thereof. In some embodiments, the compound of Formula (I) may be substituted one, two or three times, with an independently selected suitable group such as fluoromethyl, difluoromethyl or trifluoromethyl. In some embodiments, $D_1$, $D_2$, $D_3$, and $D_4$ are each hydrogen.

In some embodiments, the compound is a compound of Formula (I)(a)(1) or a compound of Formula (I)(a)(2):

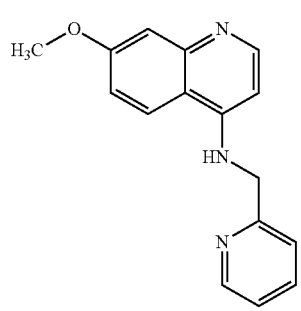
(I)(a)(1)

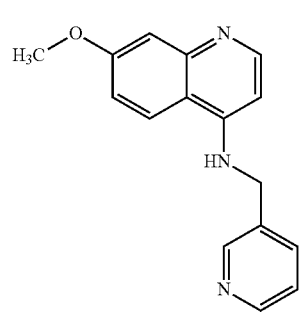
(I)(a)(2)

or a pharmaceutically acceptable salt or prodrug thereof. In some embodiments, the compound may be substituted one, two or three times, with an independently selected suitable group such as fluoromethyl, difluoromethyl or trifluoromethyl.

In some embodiments, the compound is a compound of Formula (I)(a)(1):

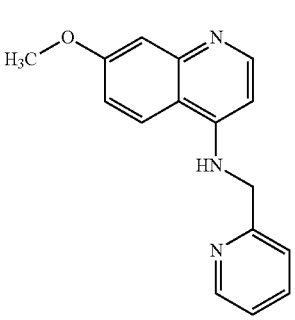
(I)(a)(1)

or a pharmaceutically acceptable salt or prodrug thereof. In some embodiments, the compound may be substituted one, two or three times, with an independently selected suitable group such as fluoromethyl, difluoromethyl or trifluoromethyl.

In some embodiments, the compound is a compound of Formula (I)(a)(2):

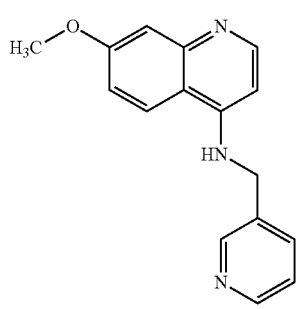

(I)(a)(2)

or a pharmaceutically acceptable salt or prodrug thereof. In some embodiments, the compound may be substituted one, two or three times, with an independently selected suitable group such as fluoromethyl, difluoromethyl or trifluoromethyl.

In some embodiments of Formula (I), $R_1$ is:

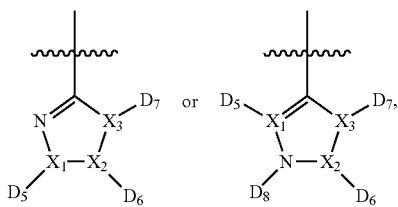

wherein $X_1$, $X_2$, and $X_3$ are each independently selected from the group consisting of carbon, nitrogen, and oxygen, and when present, $D_5$, $D_6$, $D_7$, and $D_8$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_5$, $D_6$, $D_7$, and $D_8$ together form a fused ring (e.g., a cyclohexane or cyclohexene fused ring) that is optionally substituted, or a pharmaceutically acceptable salt or prodrug thereof. In some embodiments, the compound may be substituted one, two or three times, with suitable groups such as fluoromethyl, difluoromethyl or trifluoromethyl. In some embodiments, two of $D_5$, $D_6$, $D_7$, and $D_8$ that are on adjacent atoms together form a fused ring.

In some embodiments, the compound is a compound of Formula (I)(b)(1):

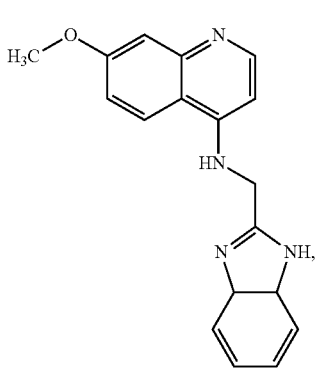

(I)(b)(1)

or a pharmaceutically acceptable salt or prodrug thereof. In some embodiments, the compound may be substituted one, two or three times, with an independently selected suitable group such as fluoromethyl, difluoromethyl or trifluoromethyl.

In some embodiments of Formula (I), $R_1$ is:

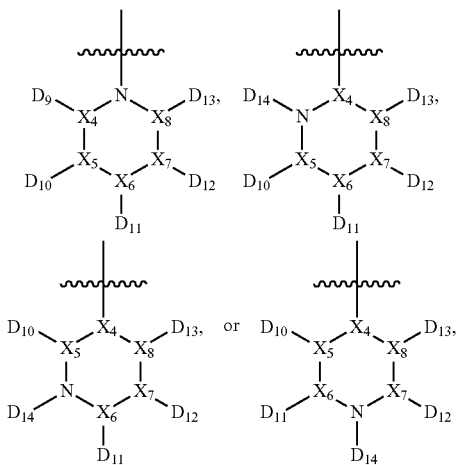

wherein $X_4$, $X_5$, $X_6$, $X_7$, and $X_8$ are each independently selected from the group consisting of carbon, nitrogen, and oxygen, wherein at least two or at least three of said $X_4$, $X_5$, $X_6$, $X_7$, and $X_8$ are carbon, and when present, $D_9$, $D_{10}$, $D_{11}$, $D_{12}$, $D_{13}$, and $D_{14}$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_9$, $D_{10}$, $D_{11}$, $D_{12}$, $D_{13}$, and $D_{14}$ together form a fused ring (e.g., a cyclohexane or cyclohexene fused ring) that is optionally substituted, or a pharmaceutically acceptable salt or prodrug thereof. In some embodiments, the compound may be substituted one, two or three times, with an independently selected suitable group such as fluoromethyl, difluoromethyl or trifluoromethyl. In some embodiments, two of $D_9$, $D_{10}$, $D_{11}$, $D_{12}$, $D_{13}$, and $D_{14}$ that are on adjacent atoms together form a fused ring.

In some embodiments of Formula (I), $R_1$ is:

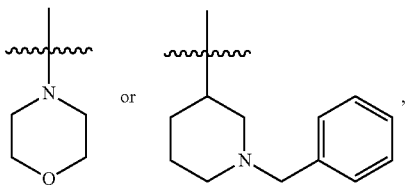 [SMILES: *N1CCOCC1 ; *C1CCCN(Cc2ccccc2)C1]

or a pharmaceutically acceptable salt or prodrug thereof.

In some embodiments, the compound may be substituted one, two or three times, with an independently selected suitable group such as fluoromethyl, difluoromethyl or trifluoromethyl.

In some embodiments of Formula (I), $R_1$ is:

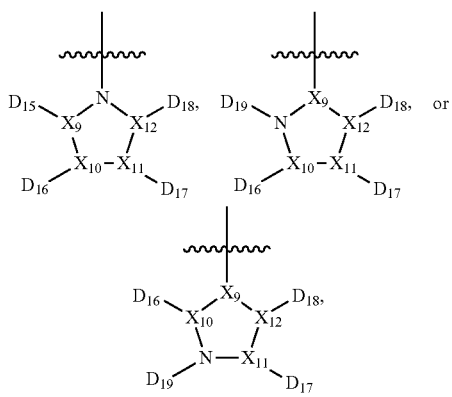

$X_9$, $X_{10}$, $X_{11}$, and $X_{12}$ are each independently selected from the group consisting of carbon, nitrogen, and oxygen, wherein at least two of said $X_9$, $X_{10}$, $X_{11}$, and $X_{12}$ are carbon, and when present, $D_{15}$, $D_{16}$, $D_{17}$, $D_{18}$, and $D_{19}$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_{15}$, $D_{16}$, $D_{17}$, $D_{18}$, and $D_{19}$ together form a fused ring (e.g., a cyclohexane or cyclohexene fused ring), optionally substituted, or a pharmaceutically acceptable salt or prodrug thereof.

In some embodiments, the compound may be substituted one, two or three times, with an independently selected suitable group such as fluoromethyl, difluoromethyl or trifluoromethyl. In some embodiments, two of $D_{15}$, $D_{16}$, $D_{17}$, $D_{18}$, and $D_{19}$ that are on adjacent atoms together form a fused ring.

In some embodiments of Formula (I), $R_1$ is:

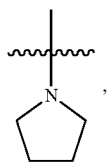 [SMILES: *N1CCCC1]

or a pharmaceutically acceptable salt or prodrug thereof.

In some embodiments, the compound may be substituted one, two or three times, with an independently selected suitable group such as fluoromethyl, difluoromethyl or trifluoromethyl.

In some embodiments, the compound has a positive log D value at approximately pH 4 to pH 5.

Unless otherwise stated, structures depicted herein are also meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Tautomeric forms include keto-enol tautomers of a compound. In addition, unless otherwise stated, all rotamer forms of the compounds of the invention are within the scope of the invention. Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

III. Methods of Use

As noted above, active compounds as taught herein may be useful as QR2 inhibitors. Such active compounds may also be useful in the treatment of infectious diseases, cancer, immune disorders, acute neural injury and chronic neurological disorders, as well as subjects at increased risk for cerebrovascular disease. The active compounds may also be useful in the treatment of disorders associated with mitochondrial dysfunction.

Infectious diseases include, but are not limited to, parasitic infections such as malaria and amebiasis, bacterial infections such as Lyme disease, and viral infections such as those of the human immunodeficiency virus (HIV), ebola virus, chikungunya virus, dengue virus, Zika virus, etc.

Cancer treatment includes, but is not limited to, radiosensitization of cancer, chemosensitization of cancer, or a combination thereof. Cancers to be treated may include, but are not limited to, glioblastoma.

Immune disorders include, but are not limited to, autoimmune diseases. Such autoimmune diseases include, but are not limited to, lupus (systemic lupus erythematosus (SLE) and lupus nephritis); autoimmune myopathy; psoriasis; scleroderma; CREST syndrome; inflammatory myositis; Sjogren's syndrome; mixed connective tissue disease; rheumatoid arthritis; psoriatic arthritis; palindromic rheumatism; eosinophilic fasciitis; dermatomyositis; juvenile chronic arthritis, erosive osteoarthritis; calcium pyrophosphate crystal deposition disease; multiple sclerosis; inflammatory bowel disease; colitis; Crohn's disease; acute respiratory distress syndrome; pulmonary inflammation; idiopathic pulmonary fibrosis; osteoporosis; delayed hypersensitivity; autoimmune thyroiditis; Hashimoto's disease; Grave's disease; asthma; primary biliary cirrhosis; idiopathic thrombocytopenic purpura; diabetes; leucopenia; opportunistic infections; thrombus formation; arteriosclerosis; therapy-induced diseases such as antibiotic allergy, gene vector hypersensitivity, and chemotherapy-induced human antimouse antibody induction. Lupus-related autoimmune myopathy typically presents as proximal weakness and mylagias. There is also peripheral nervous system (PNS) involvement in lupus, mainly presenting as peripheral neuropathies.

Acute neural injury includes, but is not limited to, traumatic brain injury and non-traumatic acute brain injury. Traumatic brain injury, as known in the art, is damage and/or dysfunction of the brain caused by a single or repetitive external mechanical force, such as blunt force or sheer force from sudden acceleration or deceleration. Traumatic brain injury includes, but is not limited to, concussion, contusion, and hemorrhage, including parenchymal, subdural, epidural, and subarachnoid hemorrhage. Other acute neural injuries include insult from hypoxic or ischemic brain injury, e.g., from arterial stroke (focal, global), venous infarction, infection, etc.

Chronic neurological disorders include, but are not limited to, primary dementias such as Alzheimer's, vascular, dementia with Lewi bodies, frontotemporal, progressive supranuclear plasy, corticobasilar degeneration, as well as secondary dementias associated with chronic inflammatory conditions such as Behcet's disease, multiple sclerosis, SLE (CNS lupus), celiac disease, and non-celiac gluten sensitivity; movement disorders such as dystonia, amyotrophic lateral sclerosis (ALS), Parkinson's disease and Huntington's; and epilepsy. CNS lupus, in particular, may present clinically as acute confusion, fatigue, headache, subtle cognitive impairment, delirium, coma, dementia, sensory/motor/autonomic deficits, and/or seizures (the latter which occur more frequently in lupus patients than the general population). CNS lupus may also present as psychological disorders such as depression, mania, and/or psychosis. More focal neurological deficits are also possible and may occur secondary to lupus-related embolic, thrombotic or vasculitic infarction of brain and spine as well as cranial neuropathies. Pathophysiological mechanisms of CNS lupus may include cerebritis, transverse myelitis, neuritis and stroke (embolic, thrombotic, or vasculitic) of the brain or spine.

Subjects at increased risk for cerebrovascular disease include, for example, subjects with prior ischemic strokes or microhemorrhages; documented carotid or small vessel disease; vascular modifiable risk factors such as diabetes, hypercoagulable state, hypertension; non-modifiable risk factors such as age, race, family history, etc.

There is evidence that the antimalarial hydroxychloroquine may reduce incidence of cerebrovascular disease in high risk stroke patients. See, e.g., Sharma et al., "Hydroxychloroquine use is associated with decreased incident cardiovascular events in rheumatoid arthritis patients," *J. Amer. Heart Assoc.* 2016; 5:e002867; Jung et al., "The protective effect of antimalarial drugs on thrombovascular events in systemic lupus erythrematosus," *Arthritis Rheum.* 2010, 62(3):863-8; Wallace et al., "The relevance of antimalarial therapy with regard to thrombosis, hypercholesterolemia and cytokines in SLE," Lupus 1993, Suppl 1:S13-5.

Disorders known to be associated with mitochondrial dysfunction include, but are not limited to, neurogenerative diseases such as Alzheimer's disease, Parkinson's disease, Huntington's disease, amyotrophic lateral sclerosis, and Friedrich's ataxia; cardiovascular diseases such as atherosclerosis and other heart and vascular conditions; diabetes and metabolic syndrome; autoimmune diseases such as multiple sclerosis, systemic lupus erythematosus, and type 1 diabetes; neurobehavioral and psychiatric diseases such as autism, schizophrenia, bipolar disorder and mood disorders; gastrointestinal disorders; fatiguing disorders such as chronic fatigue syndrome and Gulf War illnesses; musculoskeletal diseases such as fibromyalgia and skeletal muscle hypertrophy/atrophy; cancer; chronic infections; etc. See, e.g., review by Nicolson, "Mitochondrial Dysfunction and Chronic Disease: Treatment With Natural Supplements," Integrative Medicine, vol. 13, no. 4, 35-43 (2014).

The term "treat" as used herein refers to any type of treatment that imparts a benefit to a subject afflicted with or at risk of an injury, disease or disorder (e.g., improvement or decreased risk of developing one or more symptoms such as cognitive dysfunction and/or motor dysfunction), delay in the progression of the injury or symptoms, etc.

In some embodiments, treatment is for prevention, for decreasing risk of developing, or for decreasing the severity or progression of an infectious disease, cancer, immune disorder, acute neural injury, or chronic neurological disorders, as well as a prophylactic treatment (i.e., decreasing the risk of development) for subjects at increased risk for cerebrovascular disease. In some embodiments, the treatment, such as a compound as taught herein, may be administered daily or otherwise in a chronic fashion to said subject.

The present invention is primarily concerned with the treatment of human subjects, but the invention may also be carried out on animal subjects, particularly mammalian subjects such as mice, rats, dogs, cats, livestock and horses for veterinary purposes, and/or for drug screening and/or drug development purposes.

IV. Formulations

In some embodiments, active compound(s) may be provided in a pharmaceutically acceptable carrier. Carriers should be acceptable in that they are compatible with any other ingredients of the formulation and not harmful to the recipient thereof. In some embodiments, the pharmaceutically acceptable carrier is a sterile (e.g., endotoxin-free or pyrogen-free water, or endotoxin-free or pyrogen-free water saline).

Formulations of the present invention may include short-term, rapid-onset, rapid-offset, controlled release, sustained release, delayed release, and pulsatile release formulations, providing the formulations achieve administration of a compound as described herein. See Remington's Pharmaceutical Sciences (18th ed.; Mack Publishing Company, Eaton, Pa., 1990), herein incorporated by reference in its entirety.

Pharmaceutical formulations according to the present invention may be suitable for various modes of delivery, including oral, parenteral (including intravenous, intramuscular, subcutaneous, intradermal, and transdermal), topical (including dermal, buccal, and sublingual), and rectal administration.

The present invention is explained in greater detail in the following non-limiting examples.

EXAMPLES

Example 1: Development of Non-Lysosomotropic Aminoquinoline Inhibitors of QR2

Chloroquine and hydroxychloroquine are lysosomotropic drugs, accumulating preferentially in cellular lysosomes. For chloroquine, the pKa of the tertiary amine nitrogen is 10.32 and that of the quinoline nitrogen is 7.29. At acidic lysomal pHs between 4 and 5.5, nearly 100% of chloroquine is doubly protonated, rendering the molecule with a 2+ charge, making it strongly hydrophilic, membrane impermeable, and thus trapped within the acidic organelle.

A quantitative treatment of this trapping phenomenon can be obtained by examining the octanol-water distribution coefficient, log D, of a drug, which depicts the relative partition properties for all forms of a compound at different pH. Compounds with positive log D for a given pH are relatively lipophilic and more membrane permeable, whereas compounds with a negative log D are hydrophilic and less membrane permeable.

Figure 1B:
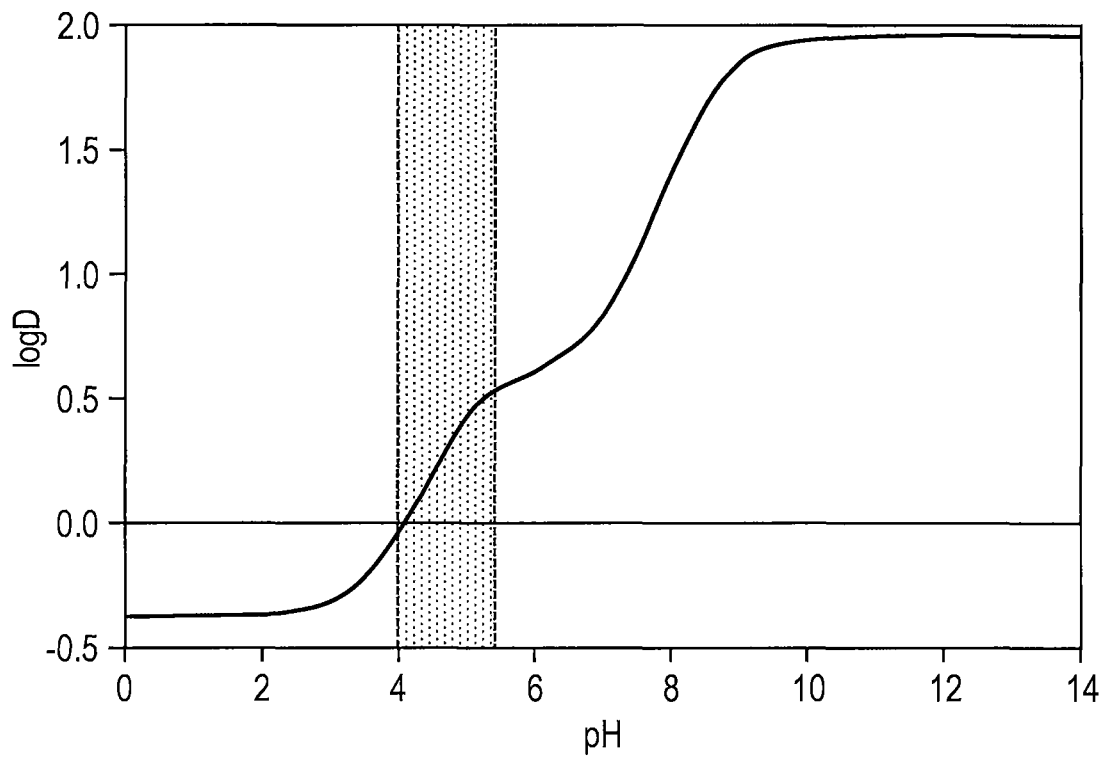

In FIG. 1A-1B the log Ds of chloroquine and QR2I-44 are shown. The shaded regions in the figures represent the potential range of lysosomal pH encountered in vivo. At lysosomal pH, the log D of chloroquine is negative, reflecting the accumulated charge of these molecules at these pH and loss of membrane permeability. For QR2i-44, however, the log D remains positive over the range of lysosomal pH, thereby retaining some lipophilicity and, therefore, membrane permeability.

Lysosomal accumulation is considered a primary mechanism responsible for the major toxicities (retinal, cardiac) of 4-aminoquinolines such as chloroquine and hydroxychloroquine (Plaquenil). Candidate compounds were determined with the goal of combining QR2 inhibitory properties with a low likelihood for lysosomal accumulation, using c Log P and Log D calculations and LiPE analysis.

From these analyses was found compound 7-methoxy-4-(pyridin-3-yl) methylaminoquinoline ("QR2I-44" "QR2i-44" or "1-44" herein) (structure shown below in Example 3). The log D value of this compound remains positive, indicating that it will retain lipophilicity (and thus membrane permeability) at lysosomal pH between 4 and 5. As noted above, FIG. 1A-1B shows log D of chloroquine (FIG. 1A) and QR2I-44 (FIG. 1B).

Although the 4-aminoquinoline scaffold has been investigated by several groups since the original discovery of chloroquine and hydroxychloroquine, this particular compound has not been explored previously. Previous studies may have avoided consciously extending the 4-aminoquinoline scaffold to include compounds with methoxy at the 7 position because of the extensive literature already extant discussing a requirement of a halogen substitution at the 7 position on 4-aminoquinolines for antimalarial activity (reviewed in Kaschula et al., "Structure-activity relationships in 4-aminoquinoline antiplasmodials," J Med. Chem. 2002, 45:3531-3539; Shreekant and Bhimanna, "4-aminoquinolines: An Overview of Antimalarial Chemotherapy," Med. Chem. 2016, 6:001-011).

7-halo substituted derivatives were originally shown to be much more active than unsubstituted analogs (Foley and Tilley, "Quinoline antimalarials: mechanisms of action and resistance and prospects for new agents," Pharmacol. Ther. 1998, 79: 55-87). Several other groups have shown more specifically that 7-chloro is, in fact, essential for inhibition of B-hematin formation (for example, see Vippagunta et al., "Structural specificity of chloroquine-hematin binding related to inhibition of hematin polymerization and parasite growth," J. Med. Chem. 1999, 42: 4630-4639), and that replacement of the 7-chloro group with other electron donor groups such as $NH_2$ and $OCH_3$ (methoxy) substantially weakens or eliminates inhibition of B-hematin formation and thereby, antimalarial activity.

See also: Egan T J (2006) Interactions of quinoline antimalarials with hematin in solution. J Inorg Biochem 100: 916-926; Nsumiwa, S.; Kuter, D.; Within, S.; Chibale, K.; Egan, T. J. Bioorg. Med. Chem. 2013, 21, 3738); Egan, T. J.; Hunter, R.; Kaschula, C. H.; Marques, H. M.; Misplon, A.; Walden, J. C., J. Med. Chem. 2000, 43, 283; Kaschula, C. H.; Egan, T. J.; Hunter, R.; Basilico, N.; Parapini, S.; Taramelli, D.; Pasini, E.; Monti, D. J. Med. Chem. 2002, 45, 3531.

Example 2: QR2 Inhibitor Synthesis and Characterization

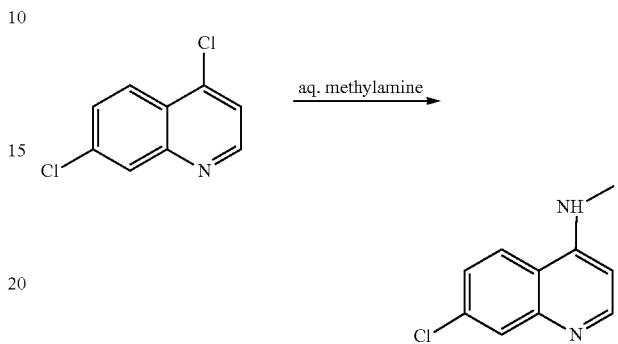

A suspension of 4,7-dichloroquinoline (2.0 g, 10.2 mmol) in aqueous methylamine (40% 20 mL 260 mmol, 26 eq.) was heated in a microwave vessel at 90° C. (initial power setting of 150 W) for 2 h. Analysis of the reaction mixture by TLC (2% MeOH in $CH_2Cl_2$) indicated complete consumption of starting material. The reaction mixture was diluted with $H_2O$ (100 mL) and insoluble were collected at the vacuum. The filter cake was washed with $H_2O$ and dried in vacuo giving the pure product as a white micro crystalline solid (1.8 g, 92%). $^1$H NMR (DMSO-$d_6$, 300 MHz) δ 8.40 (d, J=5.1 Hz, 1H), 8.16 (d, J=9.0 Hz, 1H), 7.77 (s, 1H), 6.38 (d, J=5.4 Hz, 1H), 2.86 (d, J=5.4 Hz, 3H). ESIMS: m/z=193 [(M+H)$^+$].

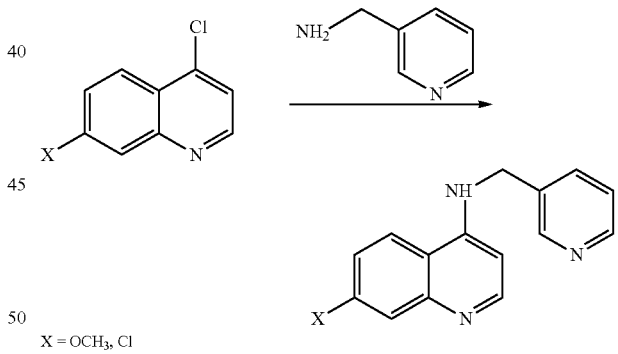

X = $OCH_3$, Cl

General procedure for 7-substituted-4-(pyridin-3-yl)-methylaminoquinolines. A mixture of the 7-substituted-4-chloroquinoline (5.1 mmol), 3-aminomethyl pyridine (0.70 g, 6.2 mmol, 1.2 eq.) and 1-butanol (5 mL) were heated in a sealed heavy walled pressure vessel (12 mL) at 130° C. (bath temperature) for 24 h. The vessel was cooled to room temperature and the contents were diluted into $Et_2O$ (150 mL). Insolubles were removed at the vacuum. The filter cake was dissolved in a minimum amount of MeOH and the resulting solution was added to silica gel (~3 g). The mixture was concentrated to dryness under reduced pressure. Flash column chromatography (RediSepR$_f$ SiO$_2$ (40 g), 100% $CH_2Cl_2$-75% (90:10, $CH_2Cl_2$:MeOH containing 10% $NH_3$) gave the desired products.

X=OCH$_3$ (pale off yellow solid, 0.60 g, 44%).

$^1$H NMR (DMSO-d$_6$, 400 MHz) δ 8.59 (s, 1H), 8.42 (m, 1H), 8.21 (d, J=5.6 Hz, 1H), 8.14 (d, J=9.2 Hz, 1H), 7.79-7.72 (m, 2H), 7.32-7.29 (m, 1H), 7.14 (m, 1H), 7.06 (dd, 2.4 Hz, 8.8 Hz, 1H), 6.25 (d, J=5.4 Hz, 1H), 4.52 (d, J=5.4 Hz, 2H), 3.84 (s, 3H). ESIMS: m/z 266 [(M+H)$^+$].

X=Cl (white solid, 0.92 g, 67%).

$^1$H NMR (DMSO-d$_6$, 400 MHz) δ 8.61 (s, 1H), 8.42 (s, 1H), 8.27 (m, 2H), 8.00 (s, 1H), 7.75 (m, 2H), 7.46 (d, J=8.8 Hz, 1H), 7.31 (m, 3H), 6.39 (d, J=5.4 Hz, 1H), 4.55 (d, J=5.4 Hz, 2H). ESIMS: m/z=270 [(M+H)$^+$].

Example 3: Comparative Testing of QR2 Inhibitors

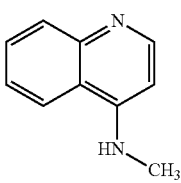

Compound 1

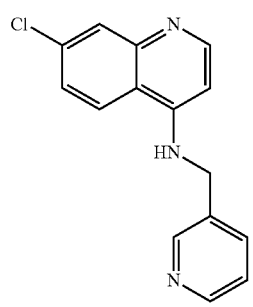

Compound 2

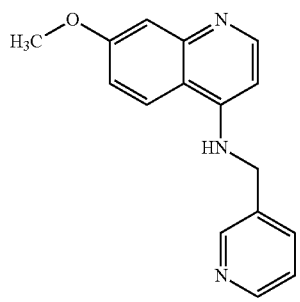

QR2I-44

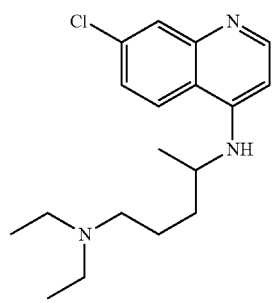

chloroquine (CQ)

TABLE 1

| comparative IC$_{50}$ data. | | |
|---|---|---|
| | IC$_{50}$ (μM) | stdev |
| QR2 I-44 | 7.51 | 0.66 |
| Compound 1 | 7.23 | 1.51 |
| Compound 2 | 15.50 | 4.84 |
| chloroquine | 70.92 | 5.27 |

We investigated the neuroprotective potential of QR2I-44 in a mouse model of closed head injury (TBI) (Laskowitz et al., "Neuroprotective pentapeptide CN-105 is associated with reduced sterile inflammation and improved functional outcomes in a traumatic brain injury murine model", Sci. Rep. 2017 Apr. 21; 7:46461; Laskowitz, et al. "Traumatic brain injury exacerbates neurodegenerative pathology: improvement with an apolipoprotein E-based therapeutic." Journal of Neurotrauma 2010m 27:1983-1995. The closed head impact model results in injury to selectively vulnerable neurons in cortex, basal ganglia, and hippocampus, induces diffuse axonal injury, and results in measurable vestibulomotor and long-term neurocognitive deficits. The TBI model involves a single impact designed to avoid skull fracture. Injury is produced predominantly through acceleration/deceleration forces. For this model, therapeutic compounds were delivered i.p. at 4 hours following TBI, and then once weekly thereafter for the duration of the experiment, which terminated after 28 days following assessment of spatial learning and memory.

Figure 2A:
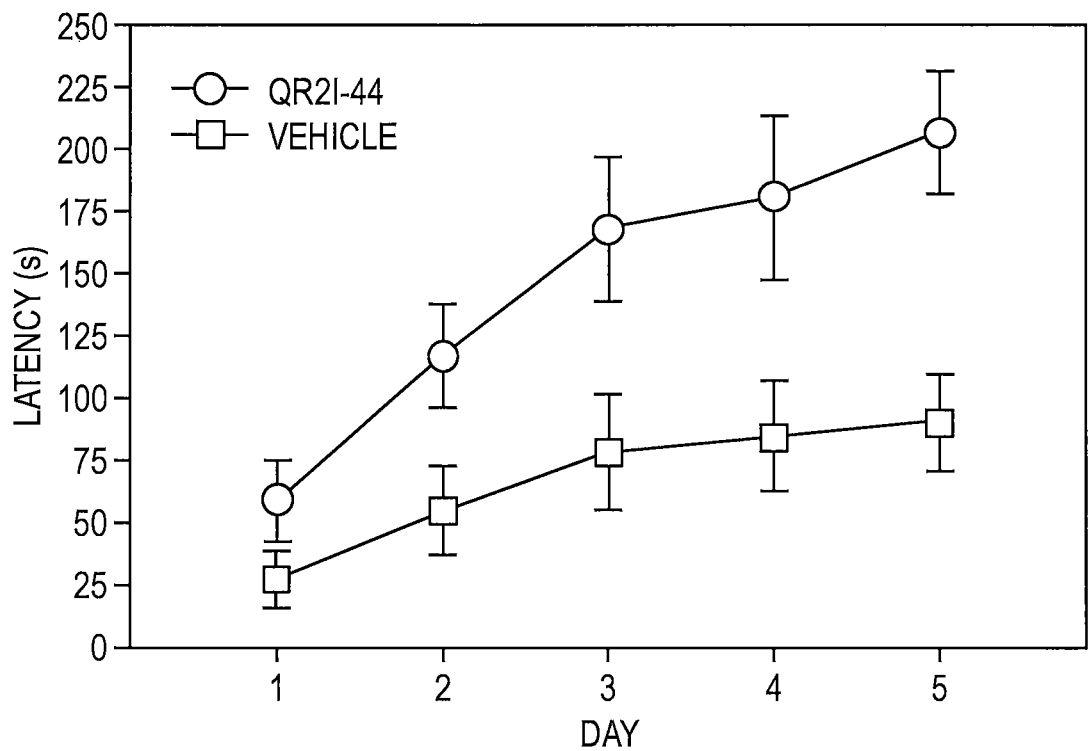
FIG. 2A-FIG. 2B.
Figure 2B:
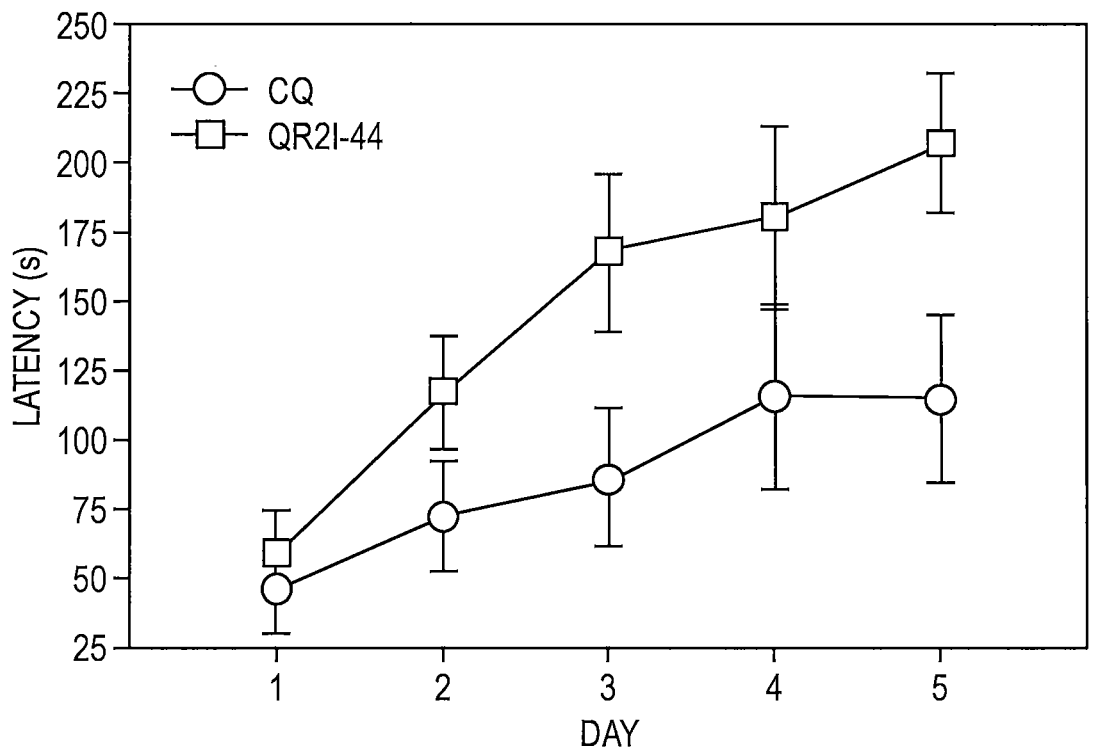
Figure 3:
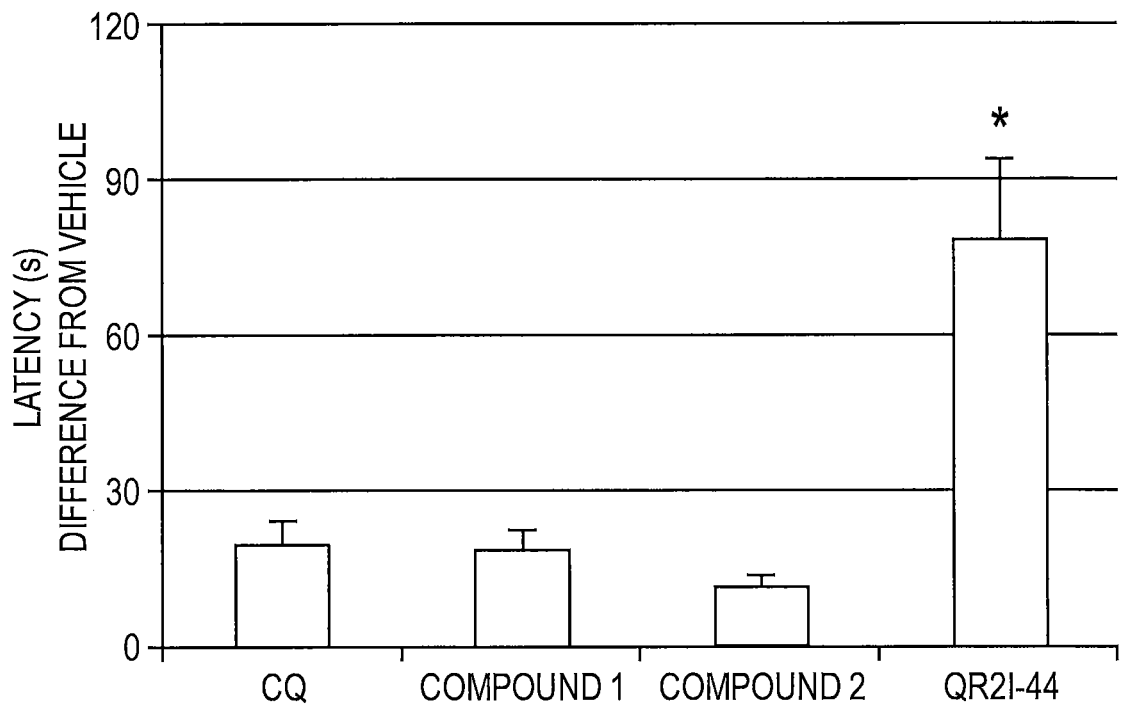
FIG. 3 presents results of comparative testing of chloroquine (CQ), Compound 1, Compound 2, and QR2I-44 in a 7 day rotorod test, confirming initial durability of QR2I-44 neuroprotection.
Figure 4:
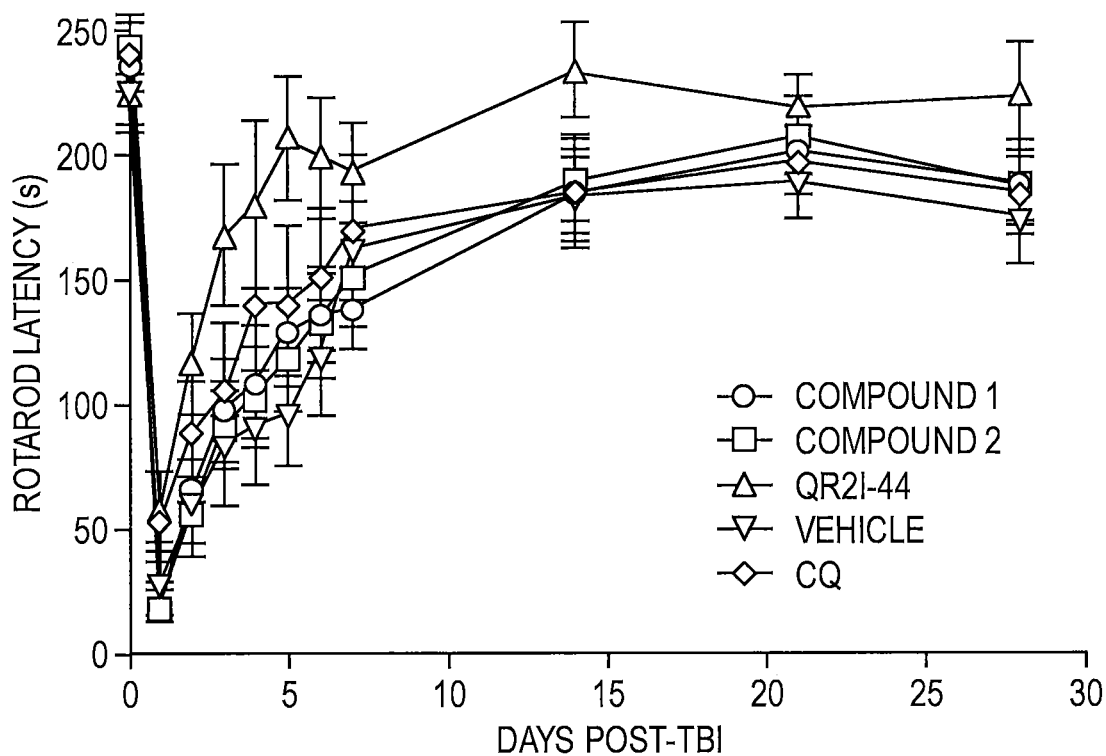
FIG. 4 presents a graph of rotorod latency versus time post-traumatic brain injury (TBI) for chloroquine (CQ), Compound 1, Compound 2, and QR2I-44 in a 28 day rotorod test, demonstrating the durability of QR2I-44 therapeutic efficacy nearly one month following TBI.

FIGS. 2, 3, and 4 summarize the results of vestibulomotor function assessment following TBI, comparing the therapeutic efficacy of QR2-44 to three other 4-aminoquinoline compounds that inhibit QR2 (Table 1): (7-chloro-N-methylquinolin-4-amine), which demonstrates similar inhibitory properties, and compound 2 (7-chloro-N-(pyridin-3-yl)quinolin-4-amine) as well as CQ (chloroquine), both of which are weaker QR2 inhibitors. Mice were tested on Rotorod for 5 consecutive days post TBI, then on day 7 and day 28. FIG. 2A-B show a nearly 300% improvement in Rotorod latency (time to fall from the rotating rod) in mice treated with QR2i-44 over vehicle, and a nearly 200% improvement over CQ, after 5 days. FIG. 3-4 shows that QR2I-44 results in durable improvements in vestibular motor function over the other QR2 inhibitors after 1 week and 4 weeks following TBI.

Figure 5A:
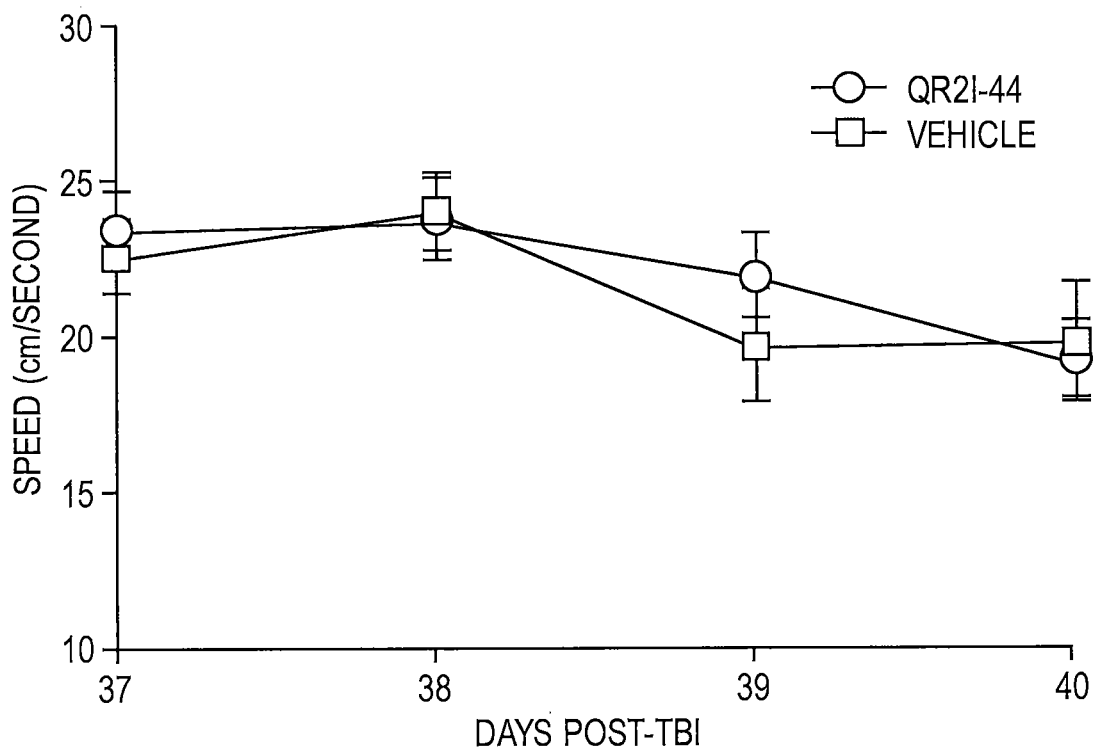
FIG. 5A-FIG. 5B.
Figure 5B:
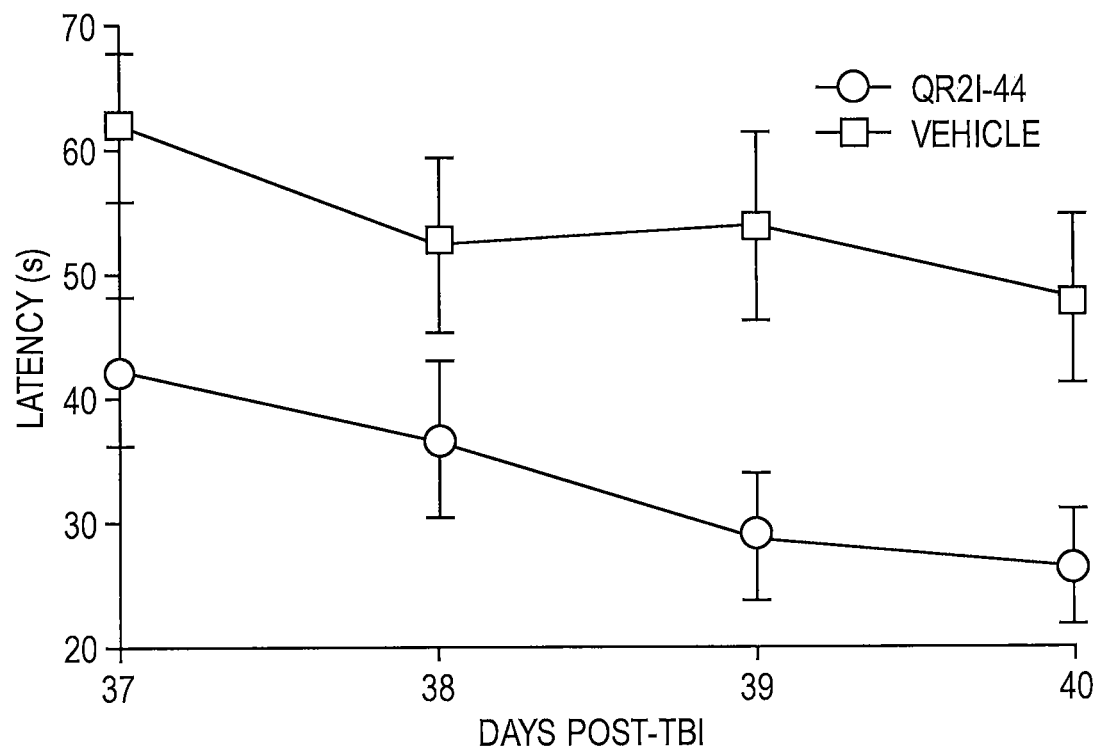

FIG. 5A-B summarize the results of spatial learning and memory assessments at 4 weeks following TBI, using the Morris Water maze to test the ability of mice to locate a submerged platform. The mice performed four trials/day for 4 consecutive days (inter-trial interval=30 min). The latency to locate the platform was recorded, and the 4 trials per day were averaged. Mice were tested on days 28-31 post-injury (n=11-12 mice per group). Standard control trials to confirm intact vision were also performed. FIG. 5B demonstrates the 30-35% improvement in learning and memory in animals treated with QR2-44 over vehicle, and FIG. 5A shows that this improvement in function is not confounded by differences in motor function (i.e., swim speed).

FIGS. 6-7 summarize the results from quantitative measurement of volumes and axonal tract integrity in brain subregions using high resolution ex vivo MRI. A total of 15 mice (10-11 week old C57Cl/6J male). Normal n=3; Vehicle n=6; QR2I-44 n=6. TBI and treatment followed the same protocol as for vestibulomotor and learning/memory assessments. Mice were sacrificed and perfused 6 weeks after TBI.

Following fixation, brains were removed from the skull and stored in 0.5% ProHance-doped formalin to facilitate high resolution MRI.

The MRI protocol comprised: (1) 3D T1-weighted FLASH sequence with FOV=1.8 cm×1.8 cm×1.8 cm; matrix=256×256×256; resolution=70×70×70 μm/pixel; TE/TR=6/30 ms; averages=16; flip-angle=34; scan time=6 hrs 33 mins; (2) High resolution spin-echo based 3D DTI with FOV=1.8 cm×1.8 cm×1.8 cm; matrix=128×128×128; resolution=141×141×141 μm/pixel; TE/TR=25/250 ms; diffusion directions=60; Ao images=5; B-value per direction=1500 S/mm2; Scan time=73 hrs 30 mins. For post-processing, mouse brains were registered to a reference template from Wake Forest University's Mouse Database and segmented using ITK-SNAP. DTI parameters were calculated using TrackVis software.

Figure 6A:
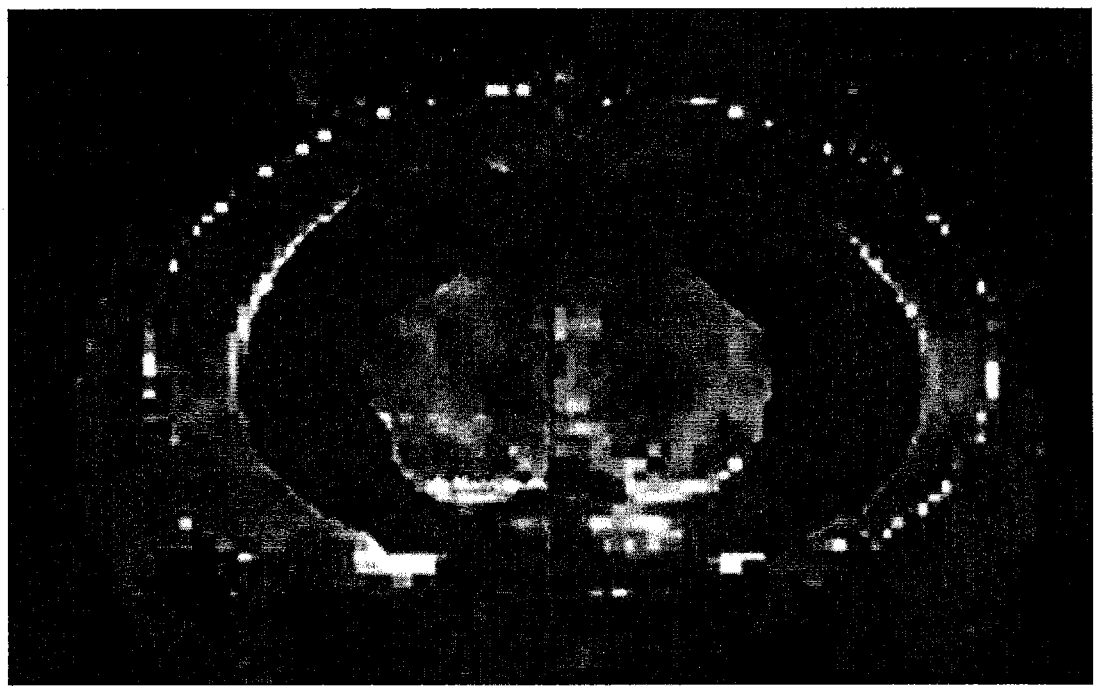
FIG. 6A-FIG. 6B.
Figure 6B:
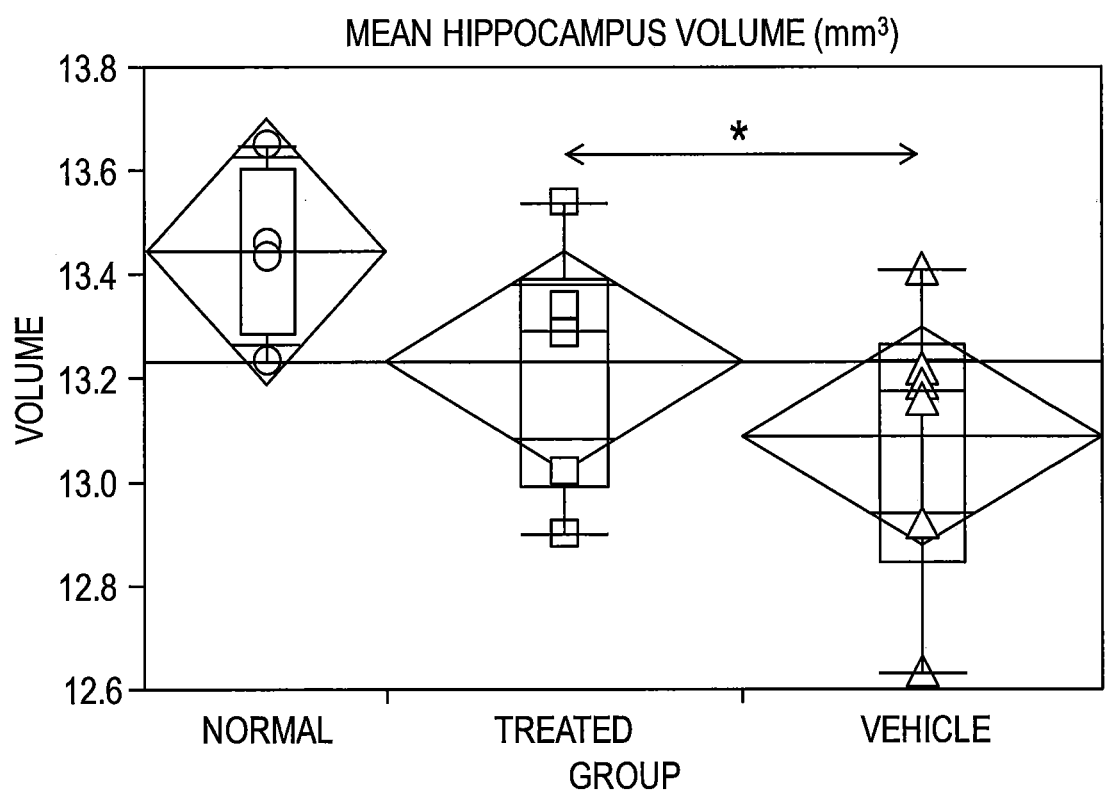
Figure 7A:
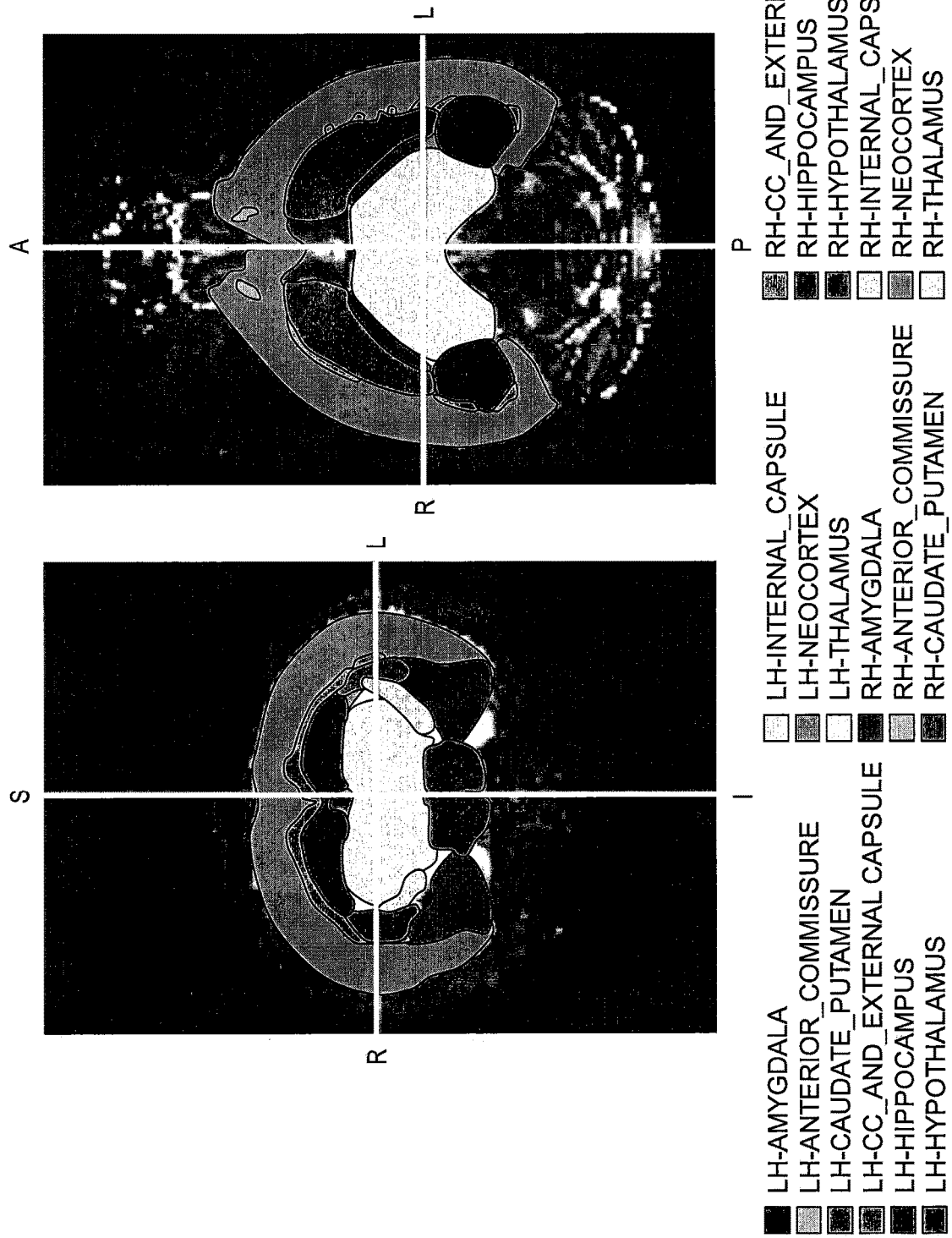
FIG. 7A-FIG. 7B.
Figure 7B:
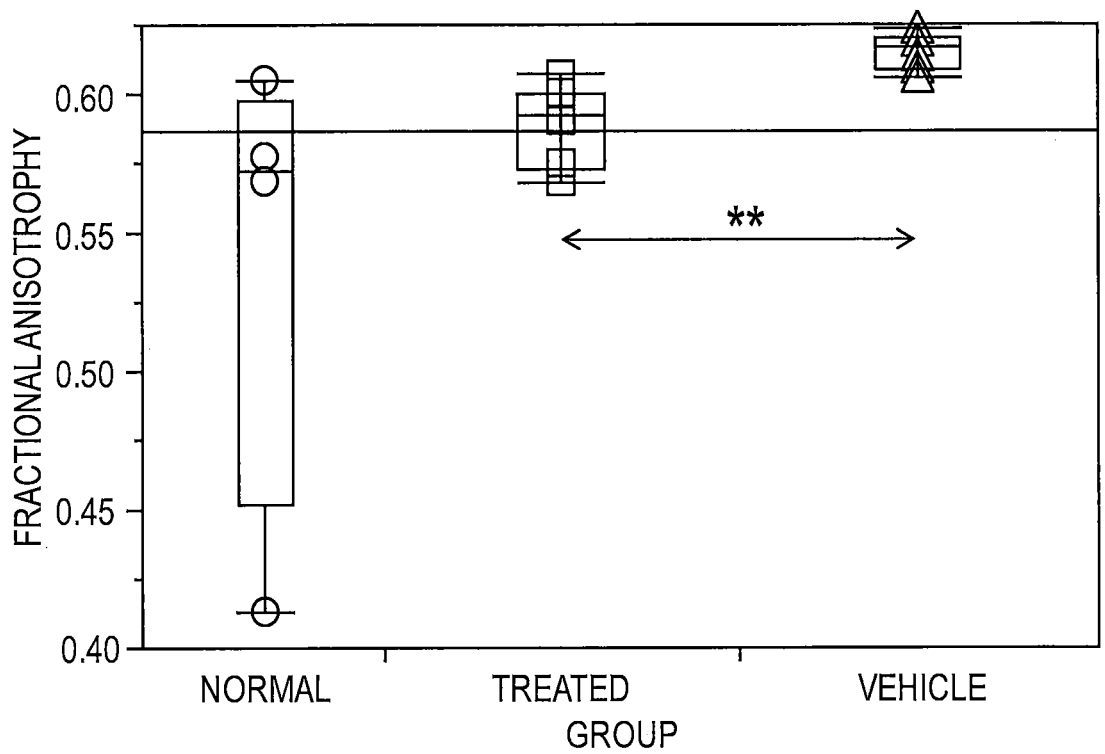

FIG. 6A-B shows that volume loss in the hippocampus following TBI is substantially mitigated in animals receiving QR2I-44 treatment as compared to vehicle control. FIG. 7A-B demonstrates that DTI parameters such as fractional anisotropy (FA), a measure of fiber tract integrity, are significantly improved following QR2I-44 therapy in large white matter track regions such as corpus collosum/external capsule (CC/EC) as compared to control.

Figure 8A:
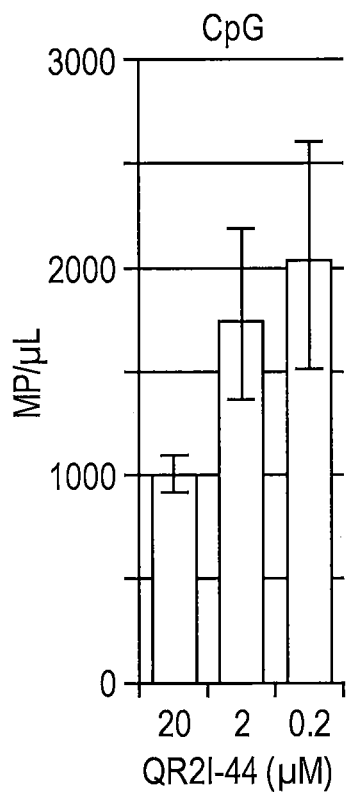
FIG. 8A-FIG. 8C.
Figure 8B:
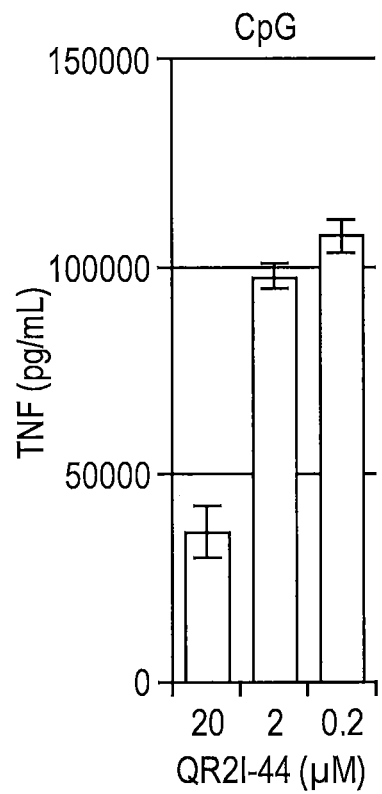
Figure 8C:
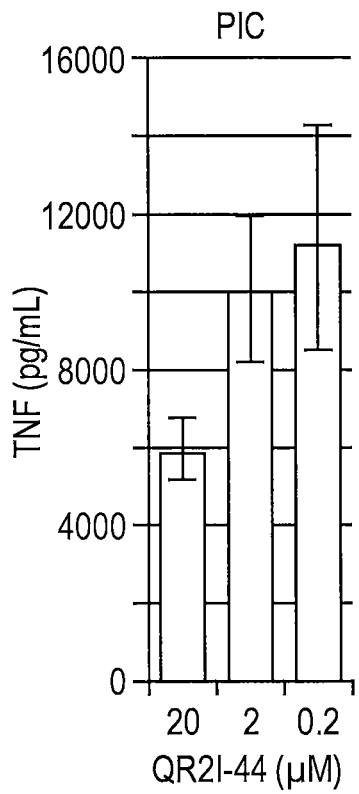

FIG. 8A-C summarizes results investigating the potential of QR2I-44 for the treatment of lupus. FIG. 8A shows the efficacy of QR2I-44 at reducing microparticle (MP) release from RAW 264.7 murine macrophage cells following stimulation with the Toll receptor ligand CpG oligodeoxynucleotide DNA (CpG.) MPs are small membrane-bound vesicles that arise from activated and dying cells by a blebbing process. These particles range in size from 0.1 to 1.0 microns and contain nuclear, cytoplasmic and membrane components. As shown in in vitro and in vivo experiments, MPs have diverse biological functions and can mediate inflammation, thrombosis and information exchange between cells among other activities. As such, MPs may play an important role in physiological and pathophysiological settings including lupus erythematosis (Spencer et al., "The Properties of Microparticles from RAW 264.7 Macrophage Cells Undergoing in vitro Activation or Apoptosis" 2014, 20(3): 239-248.)

FIG. 8B-C shows the ability of QR2I-44 to inhibit release of the inflammatory cytokine TNF alpha from RAW 264.7 murine macrophage cells following TOLL receptor ligand stimulation with CpG and PlC. In both cases, inhibition of release is dose-dependent.

Figure 9:
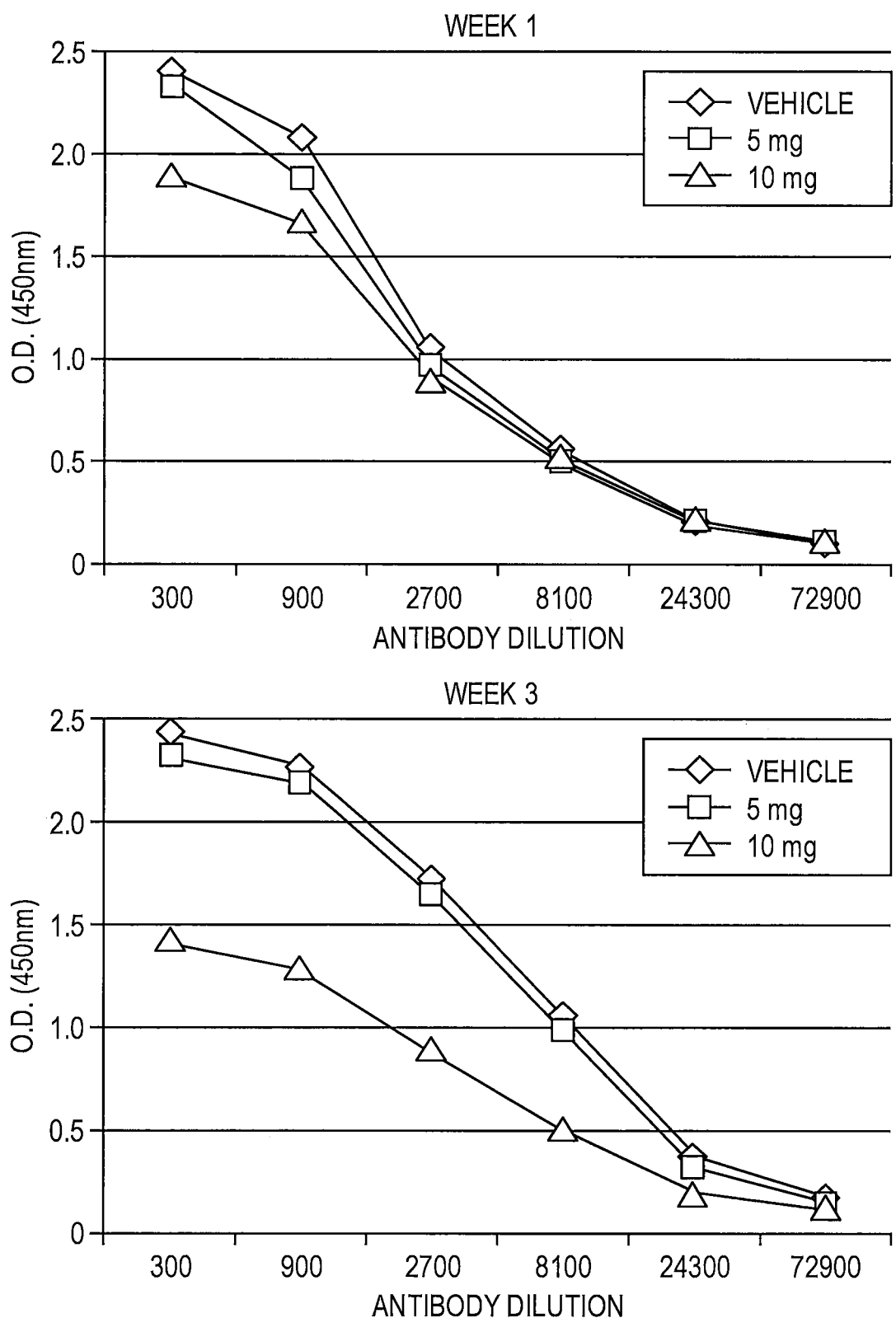
FIG. 9 shows the results of QR2I-44 treatment on anti-cDNA antibody production in mouse model of human lupus erythematosus (LPR/mrl) at one and three weeks after initiation of therapy.

FIG. 9 The MRL/lpr mouse is a well-established murine model of autoimmune disease similar to human systemic lupus erythematosus. MRL/lpr produce several biomarkers also seen in human lupus, including anti-cDNA. FIG. 9 shows the results of anti-cDNA autoantibody production in MRL/lpr mice at 1 and 3 weeks after starting QR2I-44 therapy. The comparison figures reveal gradual therapeutic inhibition of auto-antibodies in this model that is also dose-dependent.

We conducted initial screens of the drug-like properties, cardiotoxicity, mutagenicity, hepatocyte stability, and cytochrome P450 inhibition and induction of compound QR2I-44. Briefly, we found that 1-44 is not a potent inhibitor of the hERG ion channel (IC50 >10 μM), is not mutagenic in the modified Ames assay, exhibits high solubility in aqueous solutions (aqueous solubility >60 μg/ml), exhibits high membrane permeability in Caco2 cells (effective permeability >20×10−6 cm/sec), is not a P-glycoprotein substrate or inhibitor (efflux ratio <0.5; insensitive to 10 μM elacridar), low to moderate mouse and human plasma protein binding (~50-70% bound by ultracentrifugation), exhibits reasonable mouse and human hepatocyte stability (>90% remaining at 1 hour), is not an inducer or inhibitor of CYP3A4 or 2D6, and is likely to be orally bioavailable and CNS penetrant.

Example 4: Absorption and Brain Penetration of QR2i-44

In mice, QR2i-44 was found to be well absorbed and to be brain penetrant by all methods of administration, intravenous (IV), intraperitoneal (IP), and oral (PO). Shown in Table 2 below are results of PO delivery of 25 mg/kg of QR2i-44 in mouse plasma and brain samples.

TABLE 2

Mouse Plasma and Brain Sample Concentrations upon oral delivery (PO)

| Group 1 | QR2i-44 Concentrations (ng/mL) in Mouse Plasma | | | | | | | | |
|---|---|---|---|---|---|---|---|---|---|
| PO (25 mg/kg) | Rep # | | | | | | | | |
| Time (hr) | 1 | 2 | 3 | 4 | 5 | 6 | Mean | SD | % CV |
| 0.500 | 345 | 464 | 714 | 1190 | 1300 | 1120 | 856 | 403 | 47.1% |
| 6.00 | 1.16 | 2.27 | 8.52 | 59.3 | 4.28 | 2.64 | 13.0 | 22.8 | 175.1% |

| Group 1 | QR2i-44 Concentrations (ng/mL) in Mouse Brain Homogenate | | | | | | | | |
|---|---|---|---|---|---|---|---|---|---|
| PO (25 mg/kg) | Rep # | | | | | | | | |
| Time (hr) | 1 | 2 | 3 | 4 | 5 | 6 | Mean | SD | % CV |
| 0.500 | 231 | 422 | 495 | 647 | 991 | 567 | 559 | 255 | 45.6% |
| 6.00 | BQL | BQL | 5.42 | BQL | BQL | 5.08 | 5.25 | 0.240 | 4.6% |

0.5 hr samples are animals (Rep #) 1-6 respectively
6 hr samples are animals (Rep #) 7-12 respectively
BQL = Below the quantitation limit (<5.00 ng/mL)

Example 5: Crystal Structure of QR2i-44 Confirms Binding to QR2

We determined the crystal structure of reduced QR2 in complex with FADH and QR2i-44 to 1.60 Å resolution using molecular replacement. To test the impact of redox state on the enzyme structure, we also determined the structure of the oxidized complex to 1.40 Å. The structures were readily phased via molecular replacement using as a search model existing crystal structures of QR2. The quaternary structure of the enzyme was a constitutive functional homodimer as well established.

The crystal structures confirmed that QR2i-44 and related compounds with planar ring structures bind to QR2 and FADH in a mode resembling the natural substrate quinone. Further, the crystal structures show that QR2i-44-44 may have an advantage over other inhibitors of QR2 in its ability to penetrate the substrate binding site and achieve optimal stacking of planar aromatic functional groups with FAD isoalloxazine.

Example 6: QR2 Inhibition for Treatment of Mitochondrial Dysfunction

Parkinson's disease (PD) is the most common movement neurodegenerative disorder. There is a critical unmet medical need for innovative therapeutic approaches that can successfully prevent or halt PD progression, of which none currently exist. PD is characterized by progressive neurodegeneration, and clinical symptoms include both motor impairment and non-motor features such as cognitive decline. The precise mechanism underlying the pathogenesis of PD is not yet understood. However, mitochondrial dysfunction is known to be one of the key factors contributing to the pathogenesis of both sporadic and familial PD. Mitochondrial complex I activity is decreased in the brain and systemically in subjects with PD. Inhibitors of complex I, such as rotenone which is a mitochondrial toxin, when administered to rodents and non-human primates, mimic many of the behavioral, pathological and clinical features of PD. Additionally, many of the genes that have been reported to cause or increase one's risk for developing PD, have been linked to mitochondrial pathways.

The quinone reductase 2 (QR2) enzyme can contribute to oxidative damage in the mitochondria. Inhibition of this enzyme in vivo has been shown to suppress neurotoxic effects in PD models that demonstrate mitochondrial dysfunction and oxidative stress, and blocking QR2 activity may protect and restore mitochondrial function in the context of neurodegenerative diseases such as PD.

Interestingly, an association between polymorphisms in QR2 and the risk of developing human PD has been observed, and some of these polymorphisms were shown to result in increased QR2 expression, higher enzyme activity, and increased production of ROS in the presence of dopamine (Harada et al., "An association between idiopathic Parkinson's disease and polymorphisms of phase II detoxification enzymes: glutathione S-transferase M1 and quinone oxidoreductase 1 and 2," Biochem Biophys Res Commun. 2001; 288(4):887-92; Wang et al., "Association of NRH: quinone oxidoreductase 2 gene promoter polymorphism with higher gene expression and increased susceptibility to Parkinson's disease," J Gerontol A Biol Sci Med Sci. 2008; 63(2):127-34).

Consistent with pathological QR2 activity, previous studies have shown that inhibition of QR2 with drugs (e.g. chloroquine and resveratrol) are neuroprotective in different animal models of neurological injury, including PD (Boutin et al., "Quinone Reductase 2 Inhibitor: Main Biochemical and Cellular Characterization," Mol Pharmacol. 2019; 95(3):269-859-11; Janda et al., "The antidote effect of quinone oxidoreductase 2 inhibitor against paraquat-induced toxicity in vitro and in vivo," Br J Pharmacol. 2013; 168(1):46-59; Janda et al., "Parkinsonian toxin-induced oxidative stress inhibits basal autophagy in astrocytes via NQO2/quinone oxidoreductase 2: Implications for neuroprotection," Autophagy. 2015; 11(7):1063-80). For example, QR2 inhibition abrogated the PD-linked paraquat induced toxicity (Janda et al. articles, supra). Furthermore, QR2 inhibition resulted in protection against PD-linked toxin MPP+ induced neurotoxicity (Boutin et al., supra). Taken together, the role of oxidative stress, mitochondrial dysfunction, QR2 pathophysiology in PD and reports that QR2 inhibition may mediate protection against neurotoxicity by decreasing ROS levels, support the premise to develop QR2 inhibitors as a therapeutic strategy for PD (Cassagnes et al., "Oxidative stress and neurodegeneration: The possible contribution of quinone reductase 2," Free Radic Biol Med. 2018; 120:56-61).

Complex I dysfunction, mitochondrial impairment and oxidative stress are key players in the pathogenesis of PD (Sanders et al., "Oxidative damage to macromolecules in human Parkinson disease and the rotenone model," Free Radic Biol Med. 2013; 62:111-20). In fact, environmental toxicants such as rotenone and paraquat, that both cause mitochondrial dysfunction and oxidative stress, have been linked to an increase in the risk of developing human PD (Tanner et al., "Rotenone, paraquat, and Parkinson's disease," Environ Health Perspect. 2011; 119(6):866-72). As such, exposure to PD-linked toxicants is one way to model mitochondrial dysfunction and oxidative stress in cells and in vivo.

Wildtype HEK293 cells were pre-treated for 1 h with a QR2 inhibitor (CDL-1, CDL-2 or QR2i-44), exposed to menadione or vehicle for 4 h and mitochondrial membrane potential was measured.

Figure 10:
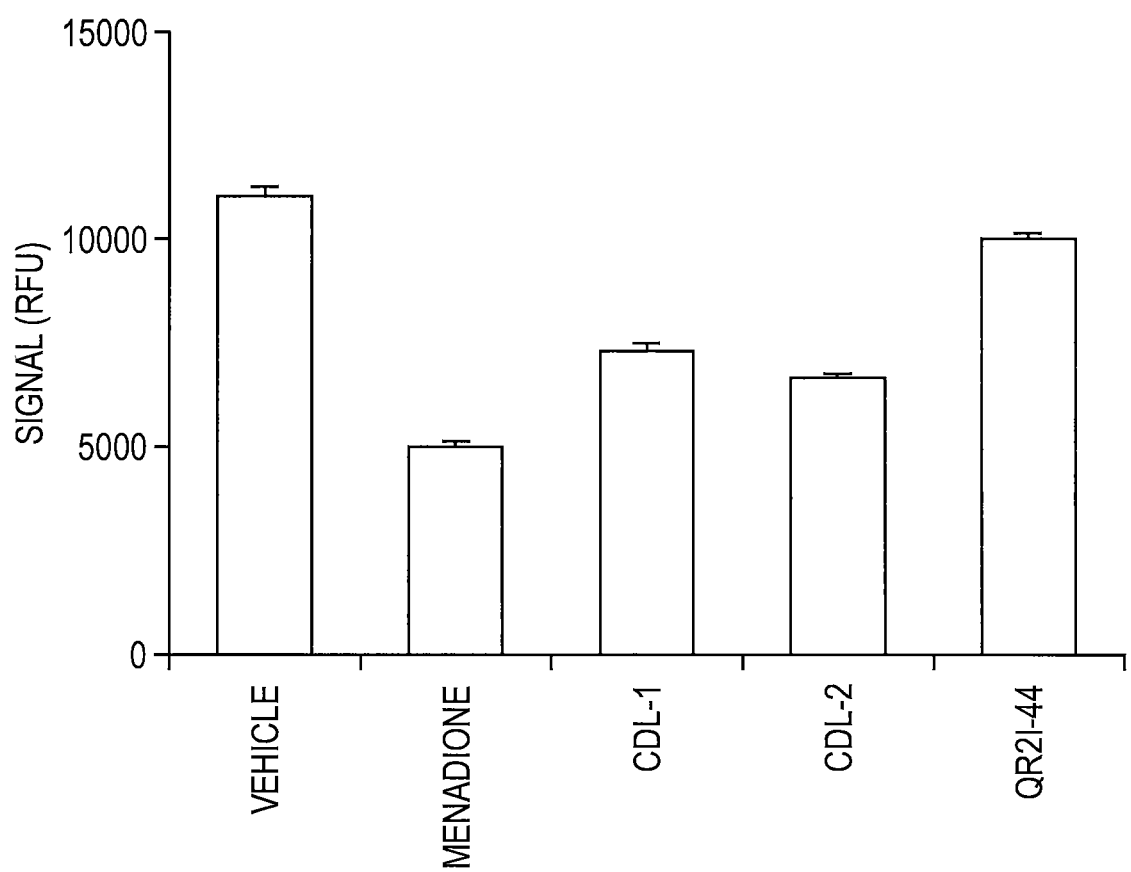
FIG. 10 presents data showing the prevention of menadione-induced loss of membrane potential by QR2 inhibitors. All QR2 inhibitors were able to prevent menadione-induced loss of membrane potential as detected by tetramethylrhodamine, ethyl ester (TMRE, a fluorescent dye sequestered by live and active mitochondria). Wildtype HEK293 cells were pre-treated for 1 h with QR2 inhibitors (CDL-1, CDL-2 and QR2i-44), then exposed to menadione for 4 h and assayed for membrane potential. QR2i-44 significantly prevented the mendione-induced loss of membrane potential.

Results: As shown in FIG. 10, all QR2 inhibitors were able to prevent menadione-induced loss of membrane potential as detected by tetramethylrhodamine, ethyl ester (TMRE, a fluorescent dye sequestered by live and active mitochondria). QR2i-44, in particular, significantly prevented the mendione-induced loss of membrane potential, and was able to prevent menadione-induced mitochondrial depolarization.

The foregoing is illustrative of the present invention, and is not to be construed as limiting thereof. The invention is defined by the following claims, with equivalents of the claims to be included therein.

That which is claimed is:
1. A compound of Formula (I):

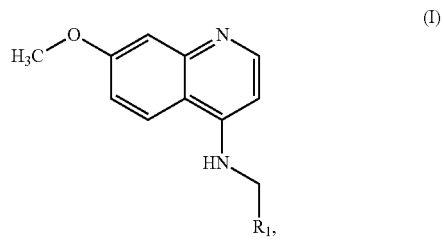

wherein $R_1$ is:

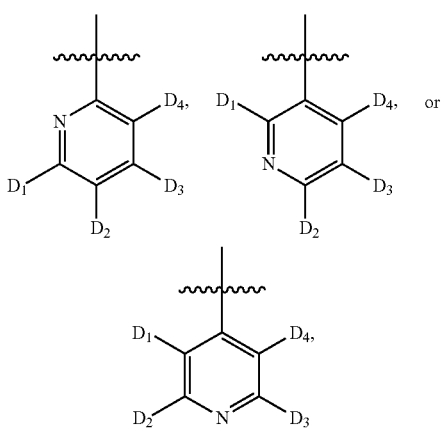

wherein $D_1$, $D_2$, $D_3$, and $D_4$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or $D_1$ and $D_2$, $D_2$ and $D_3$, or $D_3$ and $D_4$ together form a fused ring that is optionally substituted, wherein said compound is optionally substituted one, two or three times with fluoromethyl, difluoromethyl or trifluoromethyl, or a pharmaceutically acceptable salt or prodrug thereof.

2. The compound of claim 1, wherein $D_1$, $D_2$, $D_3$, and $D_4$ are each hydrogen.

3. The compound of claim 2, wherein said compound is a compound of Formula (I)(a)(1) or a compound of Formula (I)(a)(2):

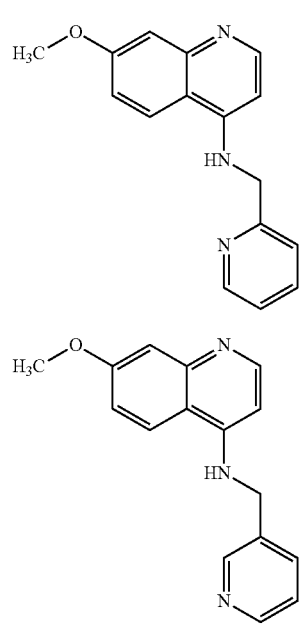

wherein said compound is optionally substituted one, two or three times with fluoromethyl, difluoromethyl or trifluoromethyl, or a pharmaceutically acceptable salt or prodrug thereof.

4. The compound of claim 2, wherein said compound is a compound of Formula (I)(a)(2):

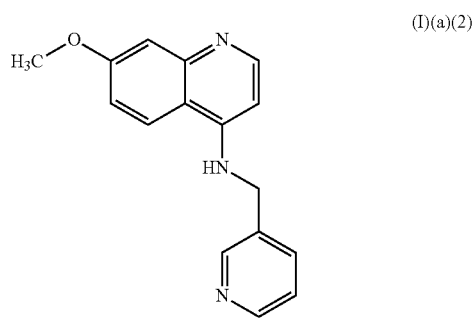

wherein said compound is optionally substituted one, two or three times with fluoromethyl, difluoromethyl or trifluoromethyl, or a pharmaceutically acceptable salt or prodrug thereof.

5. The compound of claim 2, wherein said compound is a compound of Formula (I)(a)(2):

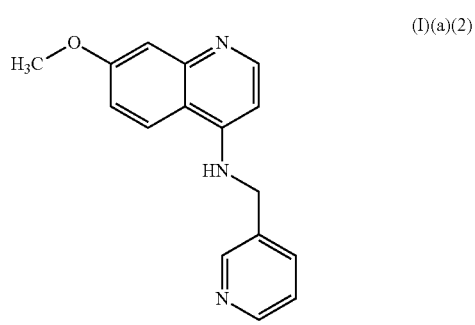 [SMILES: COc1ccc2c(NCc3cccnc3)ccnc2c1]

or a pharmaceutically acceptable salt or prodrug thereof.

6. A compound of Formula (I):

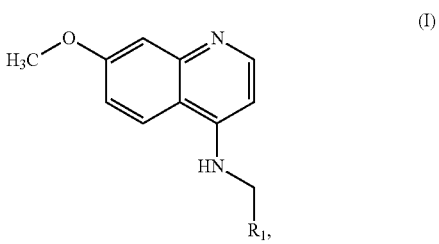

wherein $R_1$ is:

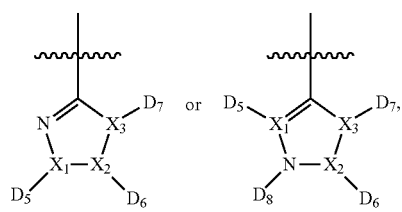

wherein $X_1$, $X_2$, and $X_3$ are each independently selected from the group consisting of carbon, nitrogen, and oxygen, and when present, $D_5$, $D_6$, $D_7$, and $D_8$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_5$, $D_6$, $D_7$, and $D_8$ together form a fused ring that is optionally substituted, wherein said compound is optionally substituted one, two or three times with fluoromethyl, difluoromethyl or trifluoromethyl, or a pharmaceutically acceptable salt or prodrug thereof.

7. The compound of claim 6, wherein said compound is a compound of Formula (I)(b)(1):

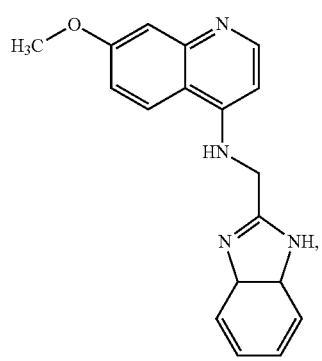

(I)(b)(1)

wherein said compound is optionally substituted one, two or three times with fluoromethyl, difluoromethyl or trifluoromethyl, or a pharmaceutically acceptable salt or prodrug thereof.

8. A compound of Formula (I):

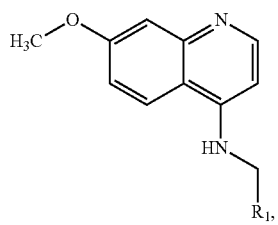

(I)

wherein $R_1$ is:

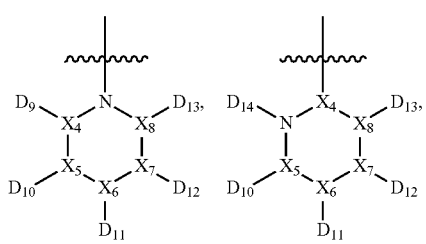

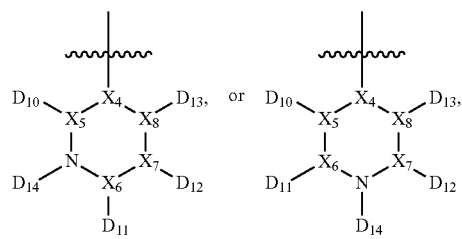

wherein $X_4$, $X_5$, $X_6$, $X_7$, and $X_8$ are each independently selected from the group consisting of carbon, nitrogen, and oxygen, wherein at least two or at least three of said $X_4$, $X_5$, $X_6$, $X_7$, and $X_8$ are carbon, and when present, $D_9$, $D_{10}$, $D_{11}$, $D_{12}$, $D_{13}$, and $D_{14}$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_9$, $D_{10}$, $D_{11}$, $D_{12}$, $D_{13}$, and $D_{14}$ together form a fused ring that is optionally substituted, or wherein $R_1$ is:

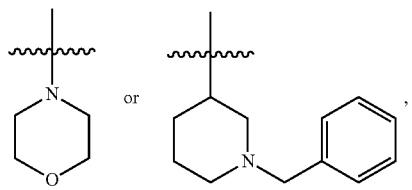 [SMILES: *N1CCOCC1 ; *C1CCCN(Cc2ccccc2)C1]

or a pharmaceutically acceptable salt or prodrug thereof.

9. The compound of claim 8, wherein $R_1$ is:

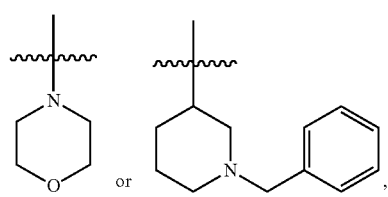 [SMILES: *N1CCOCC1 ; *C1CCCN(Cc2ccccc2)C1]

or a pharmaceutically acceptable salt or prodrug thereof.

10. A compound of Formula (I):

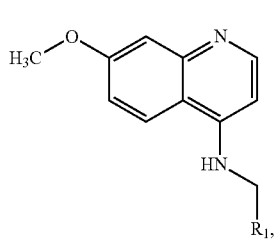

(I)

wherein $R_1$ is:

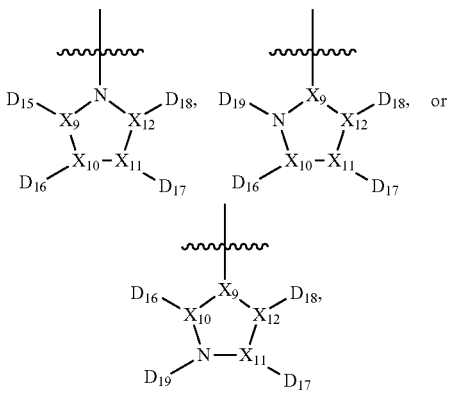

$X_9$, $X_{10}$, $X_{11}$, and $X_{12}$ are each independently selected from the group consisting of carbon, nitrogen, and oxygen, wherein at least two of said $X_9$, $X_{10}$, $X_{11}$, and $X_{12}$ are carbon, and when present, $D_{15}$, $D_{16}$, $D_{17}$, $D_{18}$, and $D_{19}$ are each independently selected from the group consisting of hydrogen, halo, alkyl, acyl, alkoxy, aryl, heteroaryl, amino, amide, nitro, hydroxyl, thiol, sulfone, sulfoxide, nitrile, nitro, and haloalkyl, or two of $D_{15}$, $D_{16}$, $D_{17}$, $D_{18}$, and $D_{19}$ together form a fused ring, optionally substituted, wherein said compound is optionally substituted one, two or three times with fluoromethyl, difluoromethyl or trifluoromethyl, or a pharmaceutically acceptable salt or prodrug thereof.

11. The compound of claim 10, wherein $R_1$ is:

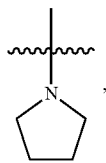 [SMILES: *N1CCCC1]

wherein said compound is optionally substituted one, two or three times with fluoromethyl, difluoromethyl or trifluoromethyl, or a pharmaceutically acceptable salt or prodrug thereof.

12. The compound of claim 1, wherein said compound has a positive log D value at approximately pH 4 to 5.

13. A composition comprising the compound of claim 1 and a carrier.

14. The composition of claim 13, wherein said carrier is a pharmaceutically acceptable carrier.

15. A method for inhibiting the activity of quinone reductase-2 (QR2), comprising contacting QR2 with the compound of claim 2.

16. The method of claim 15, wherein said contacting is performed in vitro.

17. The method of claim 15, wherein said contacting is performed in vivo.

18. A method of treatment for malaria in a subject in need thereof, comprising administering to said subject in a treatment-effective amount the compound of claim 1.

19. A method of treatment for an immune disorder in a subject in need thereof, comprising administering to said subject in a treatment-effective amount the compound of claim 1.

20. A method of treatment for lupus in a subject in need thereof, comprising administering to said subject in a treatment-effective amount the compound of claim 1.

21. A method of treatment for a disorder associated with mitochondrial dysfunction in a subject in need thereof, comprising administering to said subject in a treatment-effective amount the compound of claim 1.

22. The method of claim 15, wherein said administering comprises chronic administration.

23. The method of claim 15, wherein said administering is performed once daily.

24. The compound of claim 1, wherein $D_1$, $D_2$, $D_3$, and $D_4$ are each independently selected from the group consisting of hydrogen, halo, alkyl, aryl, heteroaryl, hydroxyl, and haloalkyl.

* * * * *

UNITED STATES PATENT AND TRADEMARK OFFICE
CERTIFICATE OF CORRECTION

| | |
|---|---|
| PATENT NO. | : 12,331,032 B2 |
| APPLICATION NO. | : 17/285622 |
| DATED | : June 17, 2025 |
| INVENTOR(S) | : Lascola et al. |

It is certified that error appears in the above-identified patent and that said Letters Patent is hereby corrected as shown below:

In the Specification

Column 9, Line 51: Please correct ""I"" to read --"/"--

Column 10, Line 45: Please correct "0, N, and S." to read --O, N, and S.--

Column 22, Line 66: Please correct "$CH_2Cl_2$-75%" to read --$CH_2Cl_2 \rightarrow 75\%$--

Column 26, Line 16: Please correct "1-44" to read --I-44--

Column 28, Lines 3-4: Please correct "NQ02/quinone" to read --NQO2/quinone--

In the Claims

Column 34, Line 15, Claim 15: Please correct "claim 2" to read --claim 1--

Signed and Sealed this
Twenty-first Day of October, 2025

John A. Squires
*Director of the United States Patent and Trademark Office*